United States Patent [19]

Woodward et al.

[11] Patent Number: 4,550,162

[45] Date of Patent: * Oct. 29, 1985

[54] PROCESS FOR THE MANUFACTURE OF ENOL DERIVATIVES

[75] Inventors: Robert E. Woodward, Cambridge, Mass.; Hans Bickel, Binningen, Switzerland

[73] Assignee: Ciba-Geigy Corporation, Ardsley, N.Y.

[*] Notice: The portion of the term of this patent subsequent to Aug. 29, 1995 has been disclaimed.

[21] Appl. No.: 430,071

[22] Filed: Sep. 30, 1982

Related U.S. Application Data

[60] Continuation of Ser. No. 323,147, Nov. 19, 1981, Pat. No. 4,434,287, which is a division of Ser. No. 36,483, May 7, 1979, Pat. No. 4,319,027, which is a continuation of Ser. No. 913,429, Jun. 7, 1978, abandoned, which is a division of Ser. No. 671,193, Feb. 10, 1976, Pat. No. 4,110,533.

[51] Int. Cl.[4] .................. C07D 501/02; A61K 31/545; C07D 501/38
[52] U.S. Cl. ....................................... 544/016; 544/22; 544/25; 544/27; 260/239 A
[58] Field of Search ...................... 544/16, 25, 21, 22, 544/26, 27; 424/246

[56] References Cited

U.S. PATENT DOCUMENTS

| 4,013,651 | 3/1977 | Spitzer | 260/243 C |
| 4,036,835 | 7/1977 | Foglio et al. | 260/243 C |
| 4,052,408 | 10/1977 | Heusle et al. | 544/16 |
| 4,065,618 | 12/1977 | Spitzer | 544/16 |
| 4,066,641 | 1/1978 | Hamashima et al. | 544/16 |
| 4,079,181 | 7/1980 | Tsuji et at. | 544/133 |
| 4,147,864 | 4/1979 | Woodward et al. | 544/16 |
| 4,160,085 | 7/1979 | Tsuji et al. | 544/16 |

Primary Examiner—Nicholas S. Rizzo
Attorney, Agent, or Firm—Irving N. Feit

[57] ABSTRACT

The invention concerns a process for the manufacture of 7β-amino-3-cephem-3-ol-4-carboxylic acid compounds by ring closure of esters of 2-[4-(substituted-thio)-3-acylamino-2-oxoazetidin-1-yl]-3-substituted-amino-crotonic acids and solvolysing the enamine group in the resulting 7β-acylamino-3-substituted-amino-cephem-4-carboxylic acid esters.

14 Claims, No Drawings

PROCESS FOR THE MANUFACTURE OF ENOL DERIVATIVES

This is a continuation of application Ser. No. 323,147, filed on Nov. 19th, 1981, now U.S. Pat. No. 4,434,287 which is a division of Ser. No. 36,483, filed May 7th, 1979, now U.S. Pat. No. 4,319,027, which is a continuation of Ser. No. 913,429, filed June 7th, 1978, now abandoned, which is a division of Ser. No. 671,193, filed Feb. 10th, 1976, now U.S. Pat. No. 4,110,533, which claims priority of Swiss application No. 2157/75, filed Feb. 20th, 1975 and Swiss application No. 10962/75, filed Aug. 25th, 1975.

The subject of the present invention is a process for the manufacture of enol derivatives, especially 7β-amino-3-cephem-3-ol-4-carboxylic acid compounds of the formula

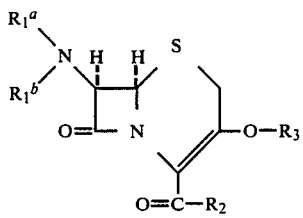

(IA)

wherein $R_1{}^a$ represents hydrogen or an amino protective group $R_1{}^A$ and $R_1{}^b$ represents hydrogen or an acyl group Ac, or $R_1{}^a$ and $R_1{}^b$ together represent a divalent amino protective group, $R_2$ represents hydroxyl or a radical $R_2{}^A$ which together with the carbonyl grouping —C(=O)— forms a protected carboxyl group and $R_3$ represents hydrogen, lower alkyl or optionally substituted α-phenyl-lower alkyl, as well as 1-oxides of 3-cephem compounds of the formula IA and the corresponding 2-cephem compounds of the formula

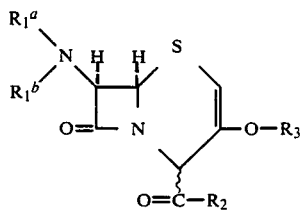

(ID)

wherein $R_1{}^a$, $R_1{}^b$, $R_2$ and $R_3$ have the abovementioned meanings, or salts of such compounds having salt-forming groups.

The enol derivatives of the present invention are ethers of 3-cephem-3-ol or 2-cephem-3-ol compounds.

In 2-cephem compounds of the formula IB having the double bond in the 2,3-position, the optionally protected carboxyl group of the formula —C(=O)—$R_2$ preferably has the α-configuration.

An amino protective group $R_1{}^A$ is a group which can be replaced by hydrogen, above all an acyl group Ac, also a triarylmethyl group, especially the trityl group, as well as an organic silyl group or an organic stannyl group. A group Ac, which can also represent a radical $R_1{}^b$, above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid), as well as the acyl radical of a carbonic acid half-derivative.

A divalent amino protective group formed by the radicals $R_1{}^a$ and $R_1{}^b$ together is, in particular, the divalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and contains, for example, two lower alkyl groups, such as methyl groups. The radicals $R_1{}^a$ and $R_1{}^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—$R_2{}^A$ is, above all, an esterified carboxyl group but can also represent an anhydride group, usually a mixed anhydride group, or an optionally substituted carbamoyl or hydrazinocarbonyl group.

The group $R_2{}^A$ can therefore be a hydroxyl group etherified by an organic radical, wherein the organic radical preferably contains up to 18 carbon atoms, which together with the —C(=O)— grouping forms an esterified carboxyl group. Examples of such organic radicals are aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2{}^A$ can also represent an organic silyloxy radical as well as a hydroxyl group etherified by an organo-metallic radical, such as an appropriate organic stannyloxy group, especially a silyloxy or stannyloxy group which is substituted by 1 to 3 optionally substituted hydrocarbon radicals, preferably with up to 18 carbon atoms, such as aliphatic hydrocarbon radicals, and is optionally substituted by halogen, such as chlorine.

A radical $R_2{}^A$ which forms, with a —C(=O)— grouping, an anhydride group, above all a mixed anhydride group, is, for example, halogen, such as chlorine, or an acyloxy radical, wherein acyl represents the corresponding radical of an organic carboxylic acid, preferably with up to 18 carbon atoms, such as of an aliphatic, cycloaliphatic, cycloaliphatic-aliphatic, aromatic or araliphatic carboxylic acid or of a carbonic acid half-derivative, such as of a carbonic acid half-ester.

A radical $R_2{}^A$ which forms, with a —C(=O)— grouping, a carbamoyl group is an optionally substituted amino group wherein substituents represent optionally substituted monovalent or divalent hydrocarbon radicals, preferably with up to 18 carbon atoms, such as optionally substituted monovalent or divalent aliphatic, cycloaliphatic, cycloaliphatic-aliphatic, aromatic or araliphatic hydrocarbon radicals with up to 18 carbon atoms, also appropriate heterocyclic or heterocyclic-aliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably contain up to 18 carbon atoms, as well as acyl radicals, above all of organic carboxylic acids and of carbonic acid half-derivatives, preferably with up to 18 carbon atoms.

In a substituted hydrazinocarbonyl group of the formula $-C(=O)-R_2^4$, one or both nitrogen atoms can be substituted, possible substituents being, above all, optionally substituted monovalent or divalent hydrocarbon radicals, preferably with up to 18 carbon atoms, such as optionally substituted, monovalent or divalent, aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, above all of organic carboxylic acids or of carbonic acid half-derivatives, preferably with up to 18 carbon atoms.

The general concepts used in the preceding and following description have, for example, the following meanings:

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, as well as lower alkenyl or lower alkinyl, and also loweer alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio, phenyl-lower alkylthio, heterocyclylthio or heterocyclyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, lower alkoxycarbonylamino, halogeno-lower alkoxycarbonylamino, optionally substituted phenyl-lower alkoxycarbonylamino, optionally substituted carbamoylamino, ureidocarbonylamino or guanidinocarbonylamino and also sulphoamino which is optionally present in the form of a salt, such as in the form of an alkali metal salt, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or cyano, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be in the form of a salt, such as in the form of an alkali metal salt.

A divalent aliphatic radical, including the appropriate radical of a divalent aliphatic carboxylic acid, is, for example, lower alkylene or lower alkenylene, which can optionally be monosubstituted, disubstituted or polysubstituted, for example like an aliphatic radical indicated above, and/or be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate organic carboxylic acid or an appropriate cycloaliphatic or cycloaliphatic-aliphatic ylidene radical, is an optionally substituted, monovalent or divalent, cycloaliphatic or cycloaliphatic-aliphatic, hydrocarbon radical, for example monocyclic, bicyclic or polycyclic cycloalkyl or cycloalkenyl, and also cycloalkylidene or cycloalkyl- or cycloalkenyl-lower alkyl or -lower alkenyl, as well as cycloalkyl-lower alkylidene or cycloalkenyl-lower alkylidene, wherein cycloalkyl and cycloalkylidene contain, for example, up to 12, such as 3–8, preferably 3–6, ring carbon atoms, whilst cycloalkenyl contains, for example, up to 12, such as 3–8, for example 5–8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be mono-substituted, disubstituted or polysubstituted, for example by optionally substituted aliphatic hydrocarbon radicals, such as by the abovementioned optionally substituted lower alkyl groups, or, for example like the abovementioned aliphatic hydrocarbon radicals, by functional groups.

An aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A divalent aromatic radical, for example of an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid, and also an araliphatic ylidene radical, is, for example, an optionally substituted araliphatic hydrocarbon radical, such as an aliphatic hydrocarbon radical which is optionally substituted and possesses, for example, up to three optionally substituted monocyclic, bicyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1–3 phenyl groups and to be optionally monosubstituted, disubstituted or polysubstituted in the aromatic and/or aliphatic part, for example like the above-mentioned aliphatic and cycloaliphatic radicals.

Heterocyclic groups, including those in heterocyclic-aliphatic radicals, including heterocyclic or heterocyclic-aliphatic groups in appropriate carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also appropriate partially or wholly saturated heterocyclic radicals of this nature, and such radicals can optionally be monosubstituted, disubstituted or polysubstituted, for example like the abovementioned cycloaliphatic radicals. The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the α- or β-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy and especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl as well as n-pentyl, isopentyl, n-hexyl, isohexyl or n-heptyl, whilst lower alkenyl can be, for example, vinyl, allyl, isopropenyl, 2- or 3-methallyl or 3-butenyl, lower alkinyl can be, for example, propargyl or 2-butinyl and lower alkylidene can be, for example, isopropylidene or isobutylidene.

Lower alkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by heteroatoms is, for example, oxa-lower alkylene, such as 3-oxa-1,5-pentylene, thia-lower alkylene, such as 3-thia-1,5-pentylene, or aza-lower alkylene, such as 3-lower alkyl-3-aza-1,5-pentylene, for example, 3-methyl-3-aza-1,5-pentylene.

Cycloalkyl is, for example, cyclopropyl, cyclobutyl, cyclopentyl, cyclohexyl or cycloheptyl, as well as adamantyl, cycloalkenyl is, for example, cyclopropenyl, 1-, 2- or 3-cyclopentenyl, 1-, 2- or 3-cyclohexenyl, 3-cycloheptenyl or 1,4-cyclohexadienyl, and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-athyl, -1,1-, -1,2- or -1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are, above all, optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, oxazacyclic, thiazacyclic or thiadiazacyclic radicals, such as imidazolyl, for example 2-imidazolyl, pyrimidyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl, or 1,2,4- or 1,3,4-thiadiazolyl, for example 1,2,4-thiadiazol-3-yl or 1,3,4-thiadiazol-2-yl, or bicyclic diazacyclic, oxazacyclic or thiazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The abovementioned heterocyclyl radicals can be substituted, for example by optionally substituted aliphatic or aromatic hydrocarbon radicals, especially lower alkyl, such as methyl, or phenyl which is optionally substituted, for example by halogen such as chlorine, for example phenyl or 4-chlorophenyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy, r tert.-pentoxy. These groups can be substituted, for example as in halogeno-lower alkoxy, especially 2-halogeno-lower alkoxy, for example 2,2,2-trichloro-ethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentoxy, cyclohexyloxy or adamantyloxy, phenyl-lower alkoxy is, for example, benzyloxy, 1- or 2-phenylethoxy, diphenylmethoxy or 4,4'-dimethoxy-diphenylmethoxy and heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio and phenyl-lower alkylthio is, for example, benzylthio, whilst mercapto groups etherified by heterocyclyl radicals or heterocyclyl-aliphatic radicals are especially pyridylthio, for example 4-pyridylthio, imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or arylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-lower alkyl- or N,N-di-lower alkyl-carbamoyl is, for example, N-methylcarbamoyl, N-ethylcarbamoyl, N,N-dimethylcarbamoyl or N,N-diethylcarbamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of the sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino and aza-lower alkyleneamino is, for example, piperazino or 4-methylpiperazino. Acylamino in particular represents carbamoylamino, lower alkylcarbamoylamino, such as mthylcarbamoylamino, ureidocarbonylamino, guanidinocarbonylamino, lower alkoxycarbonylamino, for example methoxycarbonylamino, ethoxycarbonylamino or tert.-butoxycarbonylamino, halogenolower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as acetylamino or propionylamino, and also phthalimido, or sulphoamino which is optionally present in the form of a salt, such as in the form of an alkali metal salt, for example in the form of the sodium salt, or in the form of the ammonium salt.

Lower alkanoyl is, for example, formyl, acetyl, propionyl or pivaloyl.

O-lower alkyl-phosphono is, for example, O-methyl- or O-ethyl-phosphono, O,O'-di-lower alkyl-phosphono is, for example, O,O-dimethyl-phosphono or O,O'-diethylphosphono, O-phenyl-lower alkyl-phosphono is, for example, O-benzylphosphono and O-lower alkyl-O'-phenyl-lower alkyl-phosphono is, for example, O-benzyl-O'-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxybenzyloxycarbonyl, diphenylmethoxycarbonyl or α-4-biphenyl-α-methyl-ethoxycarbonyl. Lower alkoxycarbonyl, wherein lower alkyl contains, for example, a monocyclic, monoazacyclic, monooxacyclic or monothiacyclic group, is, for example, furyl-lower alkoxycarbonyl, such as furfuryloxycarbonyl, or thienyl-lower alkoxycarbonyl, such as 2-thenyloxycarbonyl.

2-lower alkyl- and 2,2-di-lower alkyl-hydrazino is, for example, 2-methylhydrazino or 2,2-dimethylhydrazino, 2-lower alkoxycarbonylhydrazino is, for example, 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, preferably with up to 18 carbon atoms, contained in a N-acyl derivative, which is naturally occurring or can be prepared biosynthetically, semisynthetically or entirely synthetically and is preferably pharmacologically active, of a 6-amino-penam-3-carboxylic acid compound or 7-amino-3-cephem-4-carboxylic acid compound, or represents an easily removable acyl radical, especially of a carbonic acid half-derivative.

An acyl radical Ac contained in a pharmacologically active N-acyl derivative of a 6-amino-penam-3-carboxylic acid compound or 7-amino-3-cephem-4-carboxylic acid compound is above all a group of the formula

(A)

wherein n represents O and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, an optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ denotes hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character, $R^{II}$ denotes an optionally functionally modified, for example esterified or etherified, hydroxyl or mercapto group, such as a halogen atom, an optionally substituted amino group, an optionally functionally modified carboxyl or sulpho group, an optionally O-monosubstituted or O,O'-disubstituted phosphono group or an azido group, and $R^{III}$ represents hydrogen, or wherein n represents 1, each of the radicals $R^I$ and $R^{II}$ denotes a functionally modified, preferably etherified or esterified, hydroxyl group or an optionally functionally modified carboxyl group and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula A, for example, n represents 0 and $R^I$ represents hydrogen or a cycloalkyl group with 5–7 ring carbon atoms which is optionally substituted, preferably in the 1-position, by optionally protected amino, acylamino, wherein acyl above all represents the acyl radical of a carbonic acid half-ester, such as a lower alkoxycarbonyl, 2-halogeno-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogeno-lower alkoxycarbonyl or phenyl-lower alkoxycarbonyl radical, and/or halogen, for example chlorine, a heterocyclic group which is optionally substituted, for example by lower alkyl, for example methyl, and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or n represents 1, $R^I$ represents a lower alkyl group which is optionally substituted, preferably by halogen, such as chlorine, by phenyloxy which is optionally substituted, such as phenyloxy containing hydroxyl, acyloxy, wherein acyl has the abovementioned meaing, and/or halogen, for example chlorine, or by optionally protected amino and/or carboxyl, for example a 3-amino-3-carboxypropyl radical which has an optionally protected amino and/or carboxyl group, for example a silylated, such as tri-lower alkylsilylated, for example trimethylsilylated, amino or acylamino, such as lower alkanoylamino, halogeno-lower alkanoylamino or phthaloylamino group, and/or a silylated, such as tri-lower alkylsilylated, for example trimethylsilylated, carboxyl group, or an esterified carboxyl group, such as a carboxyl group which is esterified by lower alkyl, 2-halogeno-lower alkyl or phenyl-lower alkyl, for example diphenylmethyl, or represents a lower alkenyl group, a phenyl group which is optionally substituted, such as a phenyl group which contains hydroxyl which is optionally acylated, for example as indicated above, and/or halogen, for example chlorine, and also amino-lower alkyl, such as aminomethyl, which is optionally protected, for example acylated as indicated above, or contains phenyloxy which possesses hydroxyl which is optionally acylated, for example as indicated above, and/or halogen, for example chlorine, or represents a pyridyl, for example 4-pyridyl, pyridinium, for example 4-pyridinium, thienyl, for example 2-thienyl, furyl, for example 2-furyl, imidazolyl, for example 1-imidazolyl, or tetrazolyl, for example 1-tetrazolyl group which is optionally substituted, for example or by lower alkyl, such as methyl, or by amino or aminomethyl which are optionally protected, for example acylated as indicated above, or represents an optionally substituted lower alkoxy group, for example a methoxy group, a phenyloxy group which is optionally substituted, such as a phenyloxy group which contains optionally protected hydroxyl, for example hydroxyl acylated as indicated above, and/or halogen, such as chlorine, or represents a lower alkylthio, for example n-butylthio, or lower alkenylthio, for example allylthio group, a phenylthio, pyridylthio, for example 4-pyridylthio, 2-imidazolylthio, 1,2,4-triazol-3-ylthio, 1,3,4-triazol-2-yltio, 1,2,4-thiadiazol-3-ylthio, such as 5-methyl-1,2,4-thiadiazol-3-ylthio, 1,3,4-thiadiazol-2-ylthio, such as methyl-1,3,4-thiadiazol-2-ylthio, or 5-tetrazolylthio, such as 1-methyl-5-tetrazolylthio group, optionally substituted, for example by lower alkyl, such as methyl, or represents a halogen atom, especially a chlorine or bromine atom, an optionally functionally modified carboxyl group, such as lower alkoxycarbonyl, for example methoxycarbonyl or ethoxycarbonyl, cyano or carbamoyl which is optionally N-substituted, for example by lower alkyl, such as methyl, or phenyl, or represents an optionally substituted lower alkanoyl group, for example an acetyl or propionyl group, or a benzoyl group or an azido group, and $R^{II}$ and $R^{III}$ represent hydrogen, or n represents 1, $R^I$ represents lower alkyl or a phenyl, furyl, for example 2-furyl, thienyl, for example 2- or 3-thienyl, or isothiazolyl, for example 4-isothiazolyl group which is optionally substituted, such as substituted by hydroxyl which is optionally acylated, for example as indicated above, and/or by halogen, for example chlorine, and also represents a 1,4-cyclohexadienyl group, $R^{II}$ represents optionally protected or substituted amino, for example amino, acylamino, such as lower alkoxycarbonylamino, 2-halogeno-lower alkoxycarbonylamino or optionally substituted phenyl-lower alkoxycarbonylamino such as phenyl-lower alkoxycarbonylamino which contains lower alkoxy, for example methoxy, or nitro, for example tert.-butoxycarbonylamino, 2,2,2-trichloroethoxycarbonylamino, 4-methoxybenzyloxycarbonylamino or diphenylmethoxycarbonylamino, arylsulphonylamino, for example 4-methylphenylsulphonylamino, tritylamino, arylthioamino, such as nitrophenylthioamino, for exampe 2-nitrophenylthioamino, or tritylthioamino, or 2-propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylideneamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in a protected form, such as in an esterified form, for example as a lower alkoxycarbonyl group, for example a methoxycarbonyl group or ethoxycarbonyl group, or as a phenyloxycarbonyl group, for example a diphenylmethoxycarbonyl group, a cyano group, a sulpho group, an optionally functionally modified hydroxyl group, wherein functionally modified hydroxyl in particular represents acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy, or phenoxy, a O-lower alkyl-phosphono group or O,O'-di-lower alkyl-phosphono group, for example O-methyl-phosphono or O,O'-dimethylphosphono, or a halogen atom, for example chlorine or bromine, and $R^{III}$ represents hydrogen, or n represents 1, $R^I$ and $R^{II}$ each represent halogen, for example bromine, or lower alkoxycarbonyl, for example methoxycarbonyl, and $R^{III}$ represents hydrogen, or n represents 1, $R^I$ represents a phenyl, furyl, for example 2-furyl, or thienyl, for example 2- or 3-thienyl, or isothiazolyl, for example 4-isothiazolyl, group, which is optionally substituted, for example by hydroxyl which is optionally acylated, for example as indicated above, and/or by halogen, for example chlorine, and also represents a 1,4-cyclohexadienyl group, $R^{II}$ represents aminomethyl which is optionally protected, for example as indicated above, and $R^{III}$ represents hydrogen or n represents 1 and each of the groups $R^I$, $R^{II}$ and $R^{III}$ represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group which is optionally present in the form of a salt, or an amino group which is substituted by an acyl radical which can be split off, preferably easily, for example on treatment with an acid agent, such as trifluoroacetic acid, or by reduction, for example on treatment with a chemical reducing agent, such as zinc in the presence of aqueous acetic acid, or catalytic hydrogen, or hydrolytically, or an acyl radical which can be converted into such a radical, preferably a suitable acyl radical of a carbonic acid half-ester, such as lower alkoxycarbonyl, for example tert.-butoxycarbonyl, 2-halogeno-lower alkoxycarbonyl, for example 2,2,2-trichloroethoxycarbonyl, 2-bromoethoxycarbonyl or 2-iodoethoxycarbonyl, arylcarbonylmethoxycarbonyl, for example phenacyloxycarbonyl, optionally substituted phenyl-lower alkoxycarbonyl, such as phenyl-lower alkoxycarbonyl containing lower alkoxy, for example methoxy, or nitro, for example 4-methoxybenzyloxycarbonyl or diphenylmethoxycarbonyl, or of a carbonic acid half-amide, such as carbamoyl or N-substituted carbamoyl, such as N-lower alkylcarbamoyl, for example N-methylcarbamoyl, as well as by trityl, also by arylthio, for example 2-nitrophenylthio, arylsulphonyl, for example 4-methylphenylsulphonyl or 1-lower alkoxycarbonyl-2-propylidene, for example 1-ethoxycarbonyl-2-propylidene), 2,6-dimethoxybenzoyl, 5,6,7,8-tetrahydronaphthoyl, 2-methoxy-1-naphthoyl, 2-ethoxy-1-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, pivaloyl, hexanoyl, octanoyl, acrylyl, crotonoyl, 3-butenoyl, 2-pentenoyl, methoxyacetyl, butylthioacetyl, allylthioacetyl, methylthioacetyl, chloroacetyl, bromoacetyl, dibromoacetyl, 3-chloropropionyl, 3-bromopropionyl, aminoacetyl or 5-amino-5-carboxyvaleryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example a methyl or ethyl ester, or an aryl-lower alkyl ester, for example diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethyl-acrylyl, phenylacetyl, α-bromophenylacetyl, α-azidophenylacetyl, 3-chlorophenylacetyl, 2- or 4-aminomethyl-phenylacetyl (with an amino group which is optionally substituted, for example as indicated), phenacylcarbonyl, phenoxyacetyl, 4-trifluoromethylphenoxyacetyl, benzyloxyacetyl, phenylthioacetyl, bromophenylthioacetyl, 2-phenoxypropionyl, α-phenoxyphenylacetyl, α-methoxyphenylacetyl, α-ethoxyphenylacetyl, α-methoxy-3,4-dichlorophenylacetyl, α-cyanophenylacetyl, especially phenylglycyl, 4-hydroxyphenylglycyl, 3-chloro-4-hydroxyphenylglycyl, 3,5-dichloro-4-hydroxyphenylglycyl, α-amino-α-(1,4-cyclohexadienyl)-acetyl, α-amino-α-(1-cyclohexenyl)-acetyl, α-aminomethyl-α-phenylacetyl or α-hydroxyphenylacetyl, (it being possible, in these radicals, for an amino group which is present to be optionally substituted, for example as indicated above, and/or an aliphatic and/or phenolically bonded hydroxyl group which is present to be optionally protected, analogously to the amino group, for example by a suitable acyl radical, especially by formyl or by an acyl radical of a carbonic acid half-ester), or α-O-methyl-phosphono-phenylacetyl or α-O,O-dimethyl-phosphono-phenylacetyl, also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-amino-pyridiniumacetyl (optionally with an amino group which is substituted, for example as indicated above), 2-thienylacetyl, 3-thienylacetyl, 2-tetrahydrothienylacetyl, 2-furylacetyl, 1-imidazolylacetyl, 1-tetrazolylacetyl, α-carboxy-2-thienylacetyl or α-carboxy-3-thienylacetyl (optionally with a carboxyl group which is functionally modified, for example as indicated above), α-cyano-2-thienylacetyl, α-amino-α-(2-thienyl)-acetyl, α-amino-α-(2-furyl)-acetyl or α-amino-α-(4-isothiazolyl)-acetyl (optionally with an amino group which is substituted, for example as indicated above), α-sulphophenylacetyl (optionally with a sulpho group which is functionally modified, for example like the carboxyl group), 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl group which preferably has multiple branching and/or an aromatic substituent on the carbon atom in the α-position to the oxy group, or a methoxycarbonyl group which is substituted by arylcarbonyl, especially benzoyl, radicals, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position is preferably polysubstituted, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A divalent acyl group formed by the two radicals $R_1^A$ and $R_1^b$ is, for example, the acyl radical of a lower alkanedicarboxylic acid or lower alkenedicarboxylic acid, such as succinyl, or of a o-arylenedicarboxylic acid, such as phthaloyl.

A further divalent radical formed by the groups $R_1^A$ and $R_1^b$ is, for example, a 1-oxo-3-aza-1,4-butylene radical which is substituted, especially in the 2-position, and contains, for example, optionally substituted phenyl or thienyl, and is optionally monosubstituted or disubstituted by lower alkyl, such as methyl, in the 4-position, for example 4,4-dimethyl-2-phenyl-1-oxo-3-aza-1,4-butylene.

An etherified hydroxyl group $R_2^A$ forms, together with the carbonyl grouping, an esterified carboxyl group which can preferably be split easily or can be converted easily into another functionally modified group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^A$ which, together with a —C(=O)— grouping, forms an esterified carboxyl group which can be split particularly easily, represents, for example, 2-halogeno-lower alkoxy, wherein halogen preferably has an atomic weight of more than 19. Such a radical forms, together with the —C(=O)— grouping, an esterified carboxyl group which can be split easily on treatment with chemical reducing agents under neutral or weakly acid conditions, for example with zinc in the presence of aqueous acetic acid, or an esterified carboxyl group which can be converted easily into such a group and is, for example, 2,2,2-trichloroethoxy or 2-iodoethoxy, and also 2-chloroethoxy or 2-bromoethoxy, which can easily be converted into the latter.

An etherified hydroxyl group $R_2^A$ which, together with the —C(=O)— grouping, represents an esterified carboxyl group which can also be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group, wherein aryl in particular denotes a monocyclic, preferably substituted, aromatic hydrocarbon radical. Such a radical forms, together with the —C(=O)— grouping, an esterified carboxyl group which can be split easily on irradiation, preferably with ultraviolet light, under neutral or acid conditions. An aryl radical in such an arylmethoxy group is, in particular, lower alkoxyphenyl, for example methoxyphenyl (wherein methoxy is above all in the 3-, 4- and/or 5-position), and/or above all nitrophenyl (wherein nitro is preferably in the 2-position). Such radicals are, in particular, lower alkoxybenzyloxy, for example methoxybenzyloxy, and/or nitrobenzyloxy, above all 3- or 4-methoxybenzyloxy, 3,5-dimethoxybenzyloxy, 2-nitrobenzyloxy or 4,5-dimethoxy-2-nitrobenzyloxy.

An etherified hydroxyl group $R_2^A$ can also represent a radical which, together with the —C(=O)— grouping, forms an esterified carboxyl group which can be split easily under acid conditions, for example on treatment with trifluoroacetic acid or formic acid. Such a radical is, above all, a methoxy group, in which methyl is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group which contains electron-donating substituents or by a heterocyclic group of aromatic character which contains oxygen or sulphur as a ring member, or in which methyl denotes a ring member in a polycycloaliphatic hydrocarbon radical or denotes the ring member which represents the α-position relative to the oxygen or sulphur atom in any oxacycloaliphatic or thiacycloaliphatic radical.

Preferred polysubstituted methoxy groups of this nature are tert.-lower alkoxy, for example tert.-butoxy or tert.-pentoxy, optionally substituted diphenylmethoxy, for example diphenylmethoxy or 4,4'-dimethoxydiphenylmethoxy, and also 2-(4-biphenylyl)-2-propoxy, whilst a methoxy group which contains the abovementioned substituted aryl group or the heterocyclic group is, for example, α-lower alkoxy-phenyl-lower alkoxy, such as 4-methoxybenzyloxy or 3,4-dimethoxybenzyloxy, or furfuryloxy, such as 2-furfuryloxy. A polycycloaliphatic hydrocarbon radical in which the methyl of the methoxy group represents a branched, preferably triply branched, ring member is, for example, adamantyl, such as 1-adamantyl, and an abovementioned oxacycloaliphatic or thiacycloaliphatic radical, wherein the methyl of the methoxy group is the ring member which represents the α-position relative to the oxygen or sulphur atom denotes for example, 2-oxa- or 2-thia-lower alkylene or lower alkenylene with 5-7 ring atoms, such as 2-tetrahydrofuryl, 2-tetrahydropyranyl or 2,3-dihydro-2-pyranyl or corresponding sulphur analogues.

The radical $R_2^A$ can also represent an etherified hydroxyl group which, together with the —C(=O)— grouping, forms an esterified carboxyl group which can be split hydrolytically, for example under weakly basic or weakly acid conditions. Such a radical is preferably an etherified hydroxyl group which forms an activated ester group with the —C(=O)— grouping, such as nitrophenoxy, for example 4-nitrophenoxy or 2,4-dinitrophenoxy, nitrophenyl-lower alkoxy, for example 4-nitrobenzyloxy, hydroxy-lower alkyl-benzyloxy, for example 4-hydroxy-3,5-tert.-butyl-benzyloxy, polyhalogenophenoxy, for example 2,4,6-trichlorophenoxy or 2,3,4,5,6-pentachlorophenoxy, and also cyanomethoxy, as well as acylaminomethoxy, for example phthaliminomethoxy or succinyliminomethoxy.

The group $R_2^A$ can also represent an etherified hydroxyl group which, together with the carbonyl grouping of the formula —C(=O)—, forms an esterified carboxyl group which can be split under hydrogenolytic conditions and is, for example, α-phenyl-lower alkoxy which is optionally substituted, for example by lower alkoxy or nitro, such as benzyloxy, 4-methoxybenzyloxy or 4-nitrobenzyloxy.

The group $R_2^A$ can also be an etherified hydroxyl group which, together with the carbonyl grouping —C(=O)—, forms an esterified carboxyl group which can be split under physiological conditions, above all an acyloxymethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoyloxy-methoxy, for example acetyloxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A silyloxy or stannyloxy group $R_2^A$ preferably contains, as substituents, optionally substituted aliphatic, cycloaliphatic, aromatic or araliphatic hydrocarbon radicals, such as lower alkyl, halogeno-lower alkyl, cycloalkyl, phenyl or phenyl-lower alkyl groups, or optionally modified functional groups, such as etherified hydroxyl group, for example lower alkoxy groups, or halogen atoms, for example chlorine atoms, and above all represents tri-lower alkylsilyloxy, for example trimethylsilyloxy, halogeno-lower alkoxy-lower alkyl-silyl, for example chloro-methoxy-methyl-silyl, or tri-lower alkylstannyloxy, for example tri-n-butylstannyloxy.

An acyloxy radical $R_2^A$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy which is optionally substituted, such as by halogen, for example fluorine or chlorine, preferably in the α-position, for example acetoxy, pivalyloxy or trichloroacetoxy, or lower alkoxycarbonyloxy, for example methoxycarbonyloxy or ethoxycarbonyloxy.

A radical $R_2^A$ which, together with a —C(=O)— grouping forms an optionally substituted carbamoyl or hydrazinocarbonyl group is, for example, amino, lower alkylamino or di-lower alkylamino, such as methylamino, ethylamino, dimethylamino or diethylamino, lower alkyleneamino, for example pyrrolidino or piperidino, oxa-lower alkyleneamino, for example morpholino, hydroxylamino, hydrazino, 2-lower alkylhydrazino or 2,2-di-lower alkylhydrazino, for example 2-methylhydrazino or 2,2-dimethylhydrazino.

A lower alkyl group $R_3$ has up to 7, preferably up to 4, carbon atoms and is preferably methyl, or also ethyl, n-propyl, hexyl or heptyl.

As α-phenyl-lower alkyl, $R_3$ is, in particular, benzyl and diphenylmethyl, possible substituents of the phenyl nuclei being, for example, esterified or etherified hydroxyl, such as halogen, for example fluorine, chlorine or bromine, or lower alkoxy, such as methoxy.

Salts are, in particular, those of compounds of the formulae IA and IB having an acid grouping, such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae IA and IB which passes a basic group can also form acid addition salts, for example with inorganic acids, such as hydrochloric acid, sulphuric acid or phosphoric acid, or with suitable organic carboxylic acids or sulphonic acids, for example trifluoroacetic acid or p-toluenesulphonic acid. Compounds of the formulae IA and IB having an acid group and a basic group can also be in the form of inner salts, that is to say in the form of a zwitter-ion. 1-Oxides of compounds of the formula IA having salt-forming groups can also form salts, as described above.

The compounds of the present invention possess valuable pharmacological properties or can be used as intermediate products for the manufacture of such compounds. Compounds of the formula IA, wherein, for example, $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or wherein $R_1^a$ and $R_1^b$ together represent a 1-oxo-3-aza-1,4-butylene radical which is preferably substituted in the 2-position, for example by an aromatic or heterocyclic radical, and preferably substituted in the 4-position, for example by 2 lower alkyls, such as methyl, $R_2$ denotes hydroxyl or an etherified hydroxyl group $R_2^A$ which, together with the carbonyl group, forms an esterified carboxyl group which can be split easily under physiological conditions, and $R_3$ denotes lower alkyl, and functional groups which may be present in an acyl radical $R_1^a$, such as amino, carboxyl, hydroxyl and/or sulpho, are usually in the free form, or salts of such compounds having salt-forming groups, are effective, on parenteral and/or oral administration, against micro-organisms, such as Gram-positive bacteria, for example *Staphylococcus aureus, Streptococcus pyogenes* and *Diplococcus pneumoniae*, (for example in mice at doses of about 0.001 to about 0.02 g/kg, given subcutaneously or perorally), and Gram-negative bacteria, for example *Escherichia coli, Salmonella typhimurium, Shigella flexneri, Klebsiella pneumoniae, Enterobacter cloacae, Proteus vulgaris, Proteus rettgeri* and *Proteus mirabilis*, (for example in mice at doses of about 0.001 to about 0.15 g/kg given subcutaneously or perorally), and especially also against penicillin-resistant bacteria, and are of low toxicity. These new compounds can therefore be used, for example in the form of preparations having an antibiotic action, for the treatment of corresponding infections.

Compounds of the formula IB or 1-oxides of compounds of the formula IA, wherein $R_1{}^a$, $R_1{}^b$, $R_2$ and $R_3$ have the meanings indicated in the context of the formula IA, or compounds of the formula IA wherein $R_3$ has the abovementioned meaning and the radicals $R_1{}^a$ and $R_1{}^b$ represent hydrogen, or $R_1{}^a$ denotes an amino protective group which differs from an acyl radical occurring in pharmacologically active N-acyl derivatives of 6β-amino-penam-3-carboxylic acid compounds or 7β-amino-3-cephem-4-carboxylic acid compounds and $R_1{}^b$ denotes hydrogen, or $R_1{}^a$ and $R_1{}^b$ together represent a divalent amino protective group which differs from a 1-oxo-3-aza-1,4-butylene radical which is preferably substituted in the 2-position, for example by an aromatic or heterocyclic radical, and preferably substituted in the 4-position, for example by 2 lower alkyls, such as methyl, and $R_2$ represents hydroxyl, or $R_1{}^a$ and $R_1{}^b$ have the abovementioned meanings, $R_2$ represents a radical $R_2{}^A$ which, together with the —C(—=O)— grouping, forms a protected carboxyl group which preferably can be split easily, a carboxyl group protected in this way differing from a physiologically splittable carboxyl group, and $R_3$ has the abovementioned meanings, are valuable intermediate products which can be converted in a simple manner, for example as will be described below, into the abovementioned pharmacologically active compounds.

The invention relates in particular to the manufacture of 3-cephem compounds of the formula IA, wherein $R_1{}^a$ denotes hydrogen or preferably an acyl radical contained in a fermentatively obtainable (that is to say naturally occurring) or biosynthetically, semi-synthetically or total-synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula A, in which $R^I$, $R^{II}$, $R^{III}$ and n above all have the preferred meanings, and $R_1{}^b$ represents hydrogen, or wherein $R_1{}^a$ and $R_1{}^b$ together represent a 1-oxo-3-aza-1,4-butylene radical which is preferably substituted in the 2-position, for example by an aromatic or heterocyclic radical, such as phenyl, and preferably substituted in the 4-position, for example by two lower alkyls, such as methyl, $R_2$ represents hydroxyl, lower alkoxy which is optionally monosubstituted or polysubstituted, preferably in the α-position, for example by optionally substituted aryloxy, such as lower alkoxyphenoxy, for example 4-methoxyphenoxy, lower alkanoyloxy, for example acetoxy or pivaloyloxy, α-amino-lower alkanoyloxy, for example glycyloxy, L-valyloxy or L-leucyloxy, arylcarbonyl, for example benzoyl, or optionally substituted aryl, such as phenyl, lower alkoxyphenyl, for example 4-methoxyphenyl, nitrophenyl, for example 4-nitrophenyl, or biphenylyl, for example 4-biphenylyl, or in the β-position by halogen, for example chlorine, bromine or iodine, such as lower alkoxy, for example methoxy, ethoxy, n-propoxy, isopropoxy, n-butoxy, tert.-butoxy or tert.-pentoxy, bis-phenoxy-methoxy which is optionally substituted by lower alkoxy, for example bis-4-methoxyphenoxy-methoxy, lower alkanoyloxy-methoxy, for example acetoxymethoxy or pivaloylmethoxy, α-amino-lower alkanoyloxy-methoxy, for example glycyloxymethoxy, phenacyloxy, optionally substituted phenyl-lower alkoxy, especially 1-phenyl-lower alkoxy, such as phenylmethoxy, it being possible for such radicals to contain 1-3 phenyl radicals which are optionally substituted, for example by lower alkoxy, such as methoxy, nitro or phenyl, for example benzyloxy, 4-methoxybenzyloxy, 2-biphenylyl-2-propoxy, 4-nitro-benzyloxy, diphenylmethoxy, 4,4'-dimethoxy-diphenylmethoxy or trityloxy, or 2-halogeno-lower alkoxy, for example, 2,2,2-trichloroethoxy, 2-chloroethoxy, 2-bromoethoxy or 2-iodoethoxy, and also represents 2-phthalidyloxy, as well as acyloxy, such as lower alkoxycarbonyloxy, for example methoxycarbonyloxy or ethoxycarbonyloxy, or lower alkanoyloxy, for example acetoxy or pivaloyloxy, tri-lower alkylsilyloxy, for example trimethylsilyloxy, or amino or hydrazino which are optionally substituted, for example by lower alkyl, such as methyl, or hydroxyl, for example amino, lower alkylamino or di-lower alkylamino, such as methylamino or dimethylamino, hydrazino or 2-lower alkylhydrazino or 2,2-di-lower alkylhydrazino, for example 2-methylhydrazino or 2,2-dimethylhydrazino, or represents hydroxylamino, and $R_3$ represents hydrogen, lower alkyl, especially methyl, or benzyl or diphenylmethyl which are optionally substituted, for example by halogen or lower alkoxy, as well as the 1-oxides thereof and also the corresponding 2-cephem compounds of the formula IB, or salts of such compounds having salt-forming groups.

Above all, in a 3-cephem compound of the formula IA, and in a corresponding 2-cephem compound of the formula IB, and also in a 1-oxide of a 3-cephem compound of the formula IA, or in a salt of such a compound having salt-forming groups, $R_1{}^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, especially an acyl radical of the formula A, wherein $R^I$, $R^{II}$, $R^{III}$ and n above all have the preferred meanings, such as a phenylacetyl or phenoxyacetyl radical which is optionally substituted, for example by hydroxy, and also a lower alkanoyl or lower alkenoyl radical which is optionally substituted, for example by lower alkylthio or lower alkenylthio as well as by optionally substituted, such as acylated, amino and/or functionally modified, such as esterified, carboxyl, for example 4-hydroxyphenylacetyl, hexanoyl, octanoyl or n-butylthioacetyl, and especially 5-amino-5-carboxy-valeryl, wherein the amino groups and/or the carboxyl groups are optionally protected and are present, for example, as acylamino or, respectively, esterified carboxyl, phenylacetyl or phenoxyacetyl, or an acyl radical occurring in highly active N-acyl derivatives of 6β-amino-penam-3-carboxylic acid compounds or 7β-amino-3-cephem-4-carboxylic acid compounds, especially an acyl radical of the formula A, wherein $R^I$, $R^{II}$, $R^{III}$ and n above all have the preferred meanings, such as formyl, 2-halogeno-ethylcarbamoyl, for example 2-chloroethylcarbamoyl, cyanoacetyl, phenylacetyl, thienylacetyl, for example 2-thienylacetyl, or tetrazolylacetyl, for example 1-tetrazolylacetyl, but especially acetyl which is substituted in the α-position by a cyclic, such as a cycloaliphatic, aromatic or heterocyclic, above all monocyclic, radical and by a functional group, above all amino, carboxyl, sulpho or hydroxyl groups, especially phenylglycyl, wherein phenyl represents phenyl which is optionally substituted, for example by optionally protected hydroxyl, such as acyloxy, for example optionally halogen-substituted lower alkoxycarbonyloxy or lower alkanoyloxy, and/or by halogen, for example chlorine, for example phenyl, or 3- or 4-hydroxy-phenyl, 3-chloro-4-hydroxy-phenyl or 3,5-dichloro-4-hydroxy-phenyl (optionally also with a protected, such as acylated, hydroxyl group), and wherein the amino group can optionally also be substituted and represents, for example, a sulphoamino group which is optionally present in the form of a salt, or an amino group which contains, as substituents, a trityl group which can be split off hydrolytically, or above all an acyl group, such as an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, and also reductively, such as on treatment with a chemical reducing agent, such as zinc in the presence of aqueous acetic acid, or with catalytic hydrogen, or hydrolytically, or an acyl radical which can be converted into such a radical, preferably a suitable acyl radical of a carbonic acid half-ester, such as one of those mentioned above, for example optionally halogen-substituted or benzoyl-substituted lower alkoxycarbonyl radicals, for example tert.-butoxycarbonyl, 2,2,2-trichloroethoxycarbonyl, 2-chloroethoxycarbonyl, 2-bromoethoxycarbonyl, 2-iodoethoxycarbonyl, or phenacyloxycarbonyl, optionally lower alkoxy-substituted or nitro-substituted phenyl-lower alkoxycarbonyl, for example 4-methoxybenzoyloxycarbonyl or diphenylmethoxycarbonyl, or of a carbonic acid half-amide, such as carbamoyl or N-methylcarbamoyl, and also an arylthio or aryl-lower alkylthio radical which can be split off with a nucleophilic reagent, such as hydrocyanic acid, sulphurous acid or thioacetic acid amide, for example 2-nitrophenylthio or tritylthio, an arylsulphonyl radical which can be split off by means of electrolytic reduction, for example 4-methylphenylsulphonyl, or a 1-lower alkoxycarbonyl-2-propylidene radical or 1-lower alkanoyl-2-propylidene radical which can be split off with an acid agent, such as formic acid or an aqueous mineral acid, for example hydrochloric acid or phosphoric acid, for example 1-ethoxycarbonyl-2-propylidene, and also represents α-(1,4-cyclohexadienyl)-glycyl, α-(1-cyclohexenyl)-glycyl, α-thienylglycyl, such as α-2- or α-3-thienylglycyl, α-furylglycyl, such as α-2-furylglycyl, α-isothiazolylglycyl, such as α-4-isothiazolylglycyl, it being possible, in such radicals, for the amino group to be substituted or protected, for example as indicated for a phenylglycyl radical, and also α-carboxy-phenylacetyl or α-carboxy-thienylacetyl, for example α-carboxy-2-thienylacetyl (optionally with a functionally modified carboxyl group, for example a carboxyl group present in the form of a salt, such as in the form of a sodium salt, or in the form of an ester, such as in the form of a lower alkyl ester, for example a methyl or ethyl ester, or a phenyl-lower alkyl ester, for example a diphenylmethyl ester), α-sulpho-phenylacetyl (optionally also with a sulpho group which is functionally modified, for example like the carboxyl group), α-phosphono-, α-O-methyl-phosphono- or α-O,O'-dimethylphosphono-phenylacetyl, or α-hydroxy-phenylacetyl (optionally with a functionally modified hydroxyl group, especially with an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as one of those mentioned above, for example a lower alkoxycarbonyl radical which is optionally substituted by halogen or benzoyl, for example 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), as well as 1-aminocyclohexylcarbonyl, aminomethylphenylacetyl, such as 2- or 4-aminomethylphenylacetyl, or amino-pyridiniumacetyl, for example 4-aminopyridiniumacetyl (optionally also with an amino group which is substituted, for example as indicated above), or pyridylthioacetyl, for example 4-pyridylthioacetyl, and $R_1^b$ represents hydrogen, or $R_1^a$ and $R_1^b$ together represent a 1-oxo-3-aza-1,4-butylene radical, which is preferably substituted in the 2-position by phenyl, which is optionally substituted by protected hydroxyl, such as acyloxy, for example optionally halogen-substituted lower alkoxycarbonyloxy or lower alkanoyloxy, and/or by halogen, for example chlorine, for example phenyl, or 3- or 4-hydroxy-phenyl, 3-chloro-4-hydroxyphenyl or 3,5-dichloro-4-hydroxy-phenyl (optionally also with a protected hydroxyl group, for example a hydroxyl group acylated as indicated above) and which in the 4-position optionally contains two lower alkyl, such as methyl, and $R_2$ represents hydroxyl, lower alkoxy, especially α-poly-branched lower alkoxy, for example tert.-butoxy, and also methoxy or ethoxy, 2-halogeno-lower alkoxy, for example 2,2,2-trichloroethoxy, 2-iodoethoxy, or 2-chloroethoxy or 2-bromoethoxy which can easily be converted into the latter, phenacyloxy, 1-phenyl-lower alkoxy with 1–3 phenyl radicals, which are optionally substituted by lower alkoxy or nitro, for example 4-methoxybenzyloxy, 4-nitrobenzyloxy, diphenylmethoxy, 4,4'-dimethoxydiphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxymethoxy, lower alkoxycarbonyloxy, for example ethoxycarbonyloxy, or lower alkanoyloxy, for example acetoxy, and also tri-lower alkylsilyloxy, for example trimethylsilyloxy, and $R_3$ represents hydrogen, lower alkyl, especially methyl, or benzyl or diphenylmethyl which are optionally substituted, for example by halogen, such as chlorine or bromine, or lower alkoxy, such as methoxy.

The invention above all relates to the manufacture of 3-cephem compounds of the formula IA, wherein $R_1^a$ denotes hydrogen or an acyl group of the formula

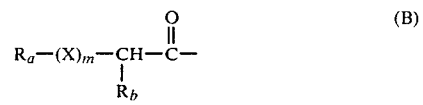

wherein $R_a$ denotes phenyl or hydroxyphenyl, for example 3- or 4-hydroxyphenyl, and also hydroxychlorophenyl, for example 3-chloro-4-hydroxyphenyl or 3,5-dichloro-4-hydroxyphenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, and also pyridyl, for example 4-pyridyl, aminopyridinium, for example 4-aminopyridinium, furyl, for example 2-furyl, isothiazolyl, for example 4-isothiazolyl, or tetrazolyl, for example 1-tetrazolyl, or also 1,4-cyclohexadienyl or 1-cyclohexenyl, X represents oxygen or sulphur, m represents 0 or 1 and $R_b$ represents hydrogen or, when m represents 0, $R_b$ represents amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino or diphenylmethoxycarbonylamino, or 3-guanylureido, and also sulphoamino or tritylamino, as well as arylthioamino, for example 2-nitrophenylthioamino, arylsulphonylamino, for example 4-methylphenylsulphonylamino, or 1-lower alkoxycarbonyl-2-propylideneamino, for example 1-ethoxycarbonyl-2-propylideneamino, carboxyl or carboxyl present in the form of a salt, for example in the form of an alkali metal salt, such as in the form of the sodium salt, as well as protected carboxyl, for example esterified carboxyl, such as phenyl-lower alkoxycarbonyl, for example diphenylmethoxycarbonyl, sulpho or sulpho present in the form of a salt, for example in the form of an alkali metal salt, such as in the form of the sodium salt, as well as protected sulpho, hydroxyl, as well as protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or O-lower alkylphosphono or O,O'-di-lower alkylphosphono, for example O-methylphosphono or O,O'-dimethylphosphono, or denotes a 5-amino-5-carboxy-valeryl radical, wherein the amino groups and/or carboxyl groups can also be protected and are present, for example, as acylamino, for example lower alkanoylamino, such as acetylamino, halogeno-lower alkanoylamino, such as dichloroacetylamino, benzoylamino or phthaloylamino, or, respectively, as esterified carboxyl, such as phenyl-lower alkoxycarbonyl, for example diphenylmethoxycarbonyl, and m preferably denotes 1 when $R_a$ represents phenyl, hydroxyphenyl, hydroxychlorophenyl or pyridyl and m denotes 0 and $R_o$ differs from hydrogen when $R_a$ represents phenyl, hydroxyphenyl, hydroxychlorophenyl, thienyl, furyl, isothiazolyl, 1,4-cyclohexadienyl or 1-cyclohexenyl, $R_1^b$ denotes hydrogen, $R_2$ above all represents hydroxyl and also represents lower alkoxy, especially α-poly-branched lower alkoxy, for example tert.-butoxy, 2-halogeno-lower alkoxy, for example 2,2,2-trichloroethoxy, 2-iodoethoxy or 2-bromoethoxy, or diphenylmethoxy which is optionally substituted, for example by lower alkoxy, for example methoxy, for example diphenylmethoxy or 4,4'-dimethoxydiphenylmethoxy, and also tri-lower alkylsilyloxy, for example trimethylsilyloxy, and $R_3$ denotes hydrogen, lower alkyl, for example methyl, ethyl or n-butyl, as well as benzyl or diphenylmethyl which is optionally substituted, for example by halogen, such as chlorine or bromine, or lower alkoxy, such as methoxy, as well as the 1-oxides of such 3-cephem compounds of the formula IA and also the corresponding 2-cephem compounds of the formula IB, or salts, especially pharmaceutically usable, non-toxic salts, of such compounds having salt-forming groups, such as alkali metal salts, for example sodium salts, or alkaline earth metal salts, for example calcium salts, or ammonium salts, including those with amines, of compounds wherein $R_2$ represents hydroxyl and which contain a free amino group in the acyl radical of the formula B.

Above all, in 3-cephem compounds of the formula IA, and also in corresponding 2-cephem compounds of the formula IB, as well as in salts, especially in pharmaceutically usable, non-toxic salts, of such compounds having salt-forming groups, as in the salts mentioned in the preceding paragraph, $R_1^a$ represents hydrogen or the acyl radical of the formula B, wherein R denotes phenyl, as well as hydroxyphenyl, for example 4-hydroxy-phenyl, thienyl, for example 2- or 3-thienyl, 4-isothiazolyl, 1,4-cyclohexadienyl or 1-cyclohexenyl, X denotes oxygen, m denotes 0 or 1 and $R_b$ denotes hydrogen or, when m denotes 0, amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino, or hydroxyl, as well as protected hydroxyl, such as acyloxy, for example, α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents a 5-amino-5-carboxyvaleryl radical, wherein the amino group and the carboxyl group can also be protected and are present, for example, as acylamino, for example lower alkanoylamino, such as acetylamino, halogeno-lower alkanoylamino, such as dichloroacetylamino, benzoylamino, or phthaloylamino, or, respectively, as esterified carboxyl, such as phenyl-lower alkoxycarbonyl, for example diphenylmethoxycarbonyl, and m perferably denotes 1 when $R_a$ is phenyl or hydroxyphenyl, $R_1^b$ represents hydrogen, $R_2$ above all denotes hydroxyl and also lower alkoxy which is optionally substituted in the 2-position by halogen, for example chlorine, bromine or iodine, especially α-poly-branched lower alkoxy, for example tert.-butoxy, or 2-halogeno-lower alkoxy, for example 2,2,2-trichloroethoxy, 2-iodoethoxy or 2-bromoethoxy, or diphenylmethoxy optionally substituted by lower alkoxy, such as methoxy, for example diphenylmethoxy, or 4,4'-dimethoxy-diphenylmethoxy, or p-nitrobenzyloxy, and also tri-lower alkylsilyloxy, for example trimethylsilyloxy, and $R_3$ denotes hydrogen, lower alkyl, especially methyl, or a benzyl or diphenylmethyl group which is optionally substituted by halogen, for example chlorine or bromine, or lower alkoxy, for example methoxy.

The invention above all serves for the manufacture of 7β-(D-α-amino-α-$R_a$-acetylamino)-3-lower alkoxy-3-cephem-4-carboxylic acids, wherein $R_a$ represents phenyl, 4-hydroxyphenyl, 2-thienyl, 1,4-cyclohexadienyl or 1-cyclohexenyl, and lower alkoxy contains up to 4 carbon atoms and represents, for example, ethoxy or n-butoxy, but above all methoxy, and the inner salts thereof, and above all of 3-methoxy-7β-(D-α-phenyl-glycylamino)-3-cephem-4-carboxylic acid and its inner salt, and for the manufacture of 3-hydroxy-3-cephem-4-carboxylic acid compounds which can serve as intermediate products for the manufacture of these 3-lower alkoxy-3-cephem-4-carboxylic acid compounds; in the abovementioned concentrations, especially on oral administration, these 3-lower alkoxy compounds display excellent antibiotic properties, both against Gram-negative and especially against Gram-negative bacteria, and are of low toxicity.

According to the process of the invention, compounds of the formula IA, their 1-oxides, compounds of the formula IB and salts of such compounds having salt-forming groups are manufactured by cyclising a compound of the formula

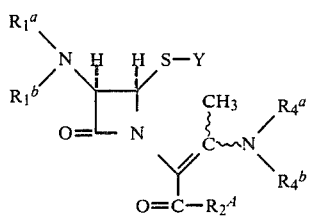

(II)

wherein $R_1^a$, $R_1^b$ and $R_2^A$ have the meanings mentioned under formula IA, the group —N($R_4^a$)($R_4^b$) represents a secondary or tertiary amino group and Y represents a leaving group, H—Y being eliminated, and solvolysing the amino group —N($R_4^a$)($R_4^b$) in the enamines, which are formed as the intermediate product, of the formula (III)

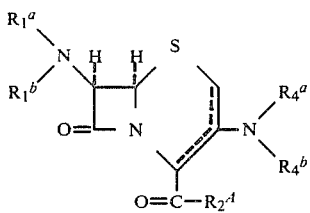

(III)

in which the double bond can be in the 2,3-position or the 3,4-position, to the —$OR_3$ group, and, if desired, in a resulting compound of the formula IA or IB, converting the protected carboxyl group of the formula —C(=O)—$R_2^A$ into the free carboxyl group or into another protected carboxyl group, and/or, if desired, converting an α-phenyl-lower alkoxy broup —O—$R_3$ into a free hydroxyl group and/or converting a resulting free hydroxyl group —O—$R_3$ into a lower alkoxy group —O—$R_3$, and/or, if desired, within the definition of the end products, converting a resulting compound into another compound, and/or, if desired, converting a resulting compound having a salt-forming group into a salt or converting a resulting salt into the free compound or into another salt and/or, if desired, separating a resulting mixture of isomeric compounds into the individual isomers.

In a compound of the formula II, the amino group —N($R_4^a$)($R_4^b$) can be in the trans-position (crotonic acid configuration) or in the cis-position (isocrotonic acid configuration) relative to the carboxyl group.

In a starting compound of the formula II, a leaving group Y is, for example, a —S—$R_4$ group, a —$SO_2$—$R_5$ group which is bonded by the sulphur atom to the thio group —S—, or a —S—$SO_2$—$R_5$ group.

In the —S—$R_4$ group, $R_4$ is an optionally substituted aromatic heterocyclic radical with up to 15, preferably up to 9, carbon atoms and at least one ring nitrogen atom and optionally a further ring hetero-atom, such as oxygen or sulphur, which radical is bonded to the thio group —S— by one of its ring carbon atoms, which is bonded to a ring nitrogen atom by a double bond. Such radicals are monocyclic or bicyclic and can be substituted, for example by lower alkyl, such as methyl or ethyl, lower alkoxy, such as methoxy or ethoxy, halogen, such as fluorine or chlorine, or aryl, such as phenyl.

Such radicals $R_4$ are, for example, monocyclic five-membered thiadiazacyclic, thiatriazacyclic, oxadiazacyclic or oxatriazacyclic radicals of aromatic character, but especially monocyclic five-membered diazacyclic, oxazacyclic and thiazacyclic radicals of aromatic character and/or, above all, the corresponding benzdiazacyclic, benzoxazacyclic or benzthiazacyclic radicals, wherein the heterocyclic part is five-membered and exhibits aromatic character, it being possible, in radicals $R_4$, for a substitutable ring nitrogen atom to be substituted, for example by lower alkyl. Representative examples of such groups $R_4$ are 1-methyl-imidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methyl-benzimidazol-2-yl, benzoxazol-2-yl and especially benzthiazol-2-yl. Further groups $R_4$ are acyl radicals of organic carboxylic or thiocarboxylic acids, such as optionally substituted, aliphatic, cycloaliphatic, araliphatic or aromatic acyl or thioacyl groups with up to 18, preferably up to 10, carbon atoms, such as lower alkanoyl, for example acetyl or propionyl, lower thioalkanoyl, for example thioacetyl, or thiopropionyl, cycloalkanecarbonyl, for example cyclohexanecarbonyl, cycloalkanethiocarbonyl, for example cyclohexanethiocarbonyl, benzoyl, thiobenzoyl, naphthylcarbonyl, naphthylthiocarbonyl, heterocyclic carbonyl or thiocarbonyl, such as 2-, 3- or 4-pyridylcarbonyl, 2- or 3-thenoyl, 2- or 3-furoyl, 2-, 3- or 4-pyridylthiocarbonyl, 2- or 3-thiothenoyl, 2- or 3-thiofuroyl or corresponding substituted acyl or thioacyl groups, for example acyl or thioacyl groups monosubstituted or polysubstituted by lower alkyl, such as methyl, halogen, such as fluorine or chlorine, lower alkoxy, such as methoxy, aryl, such as phenyl, or aryloxy, such as phenoxy.

In the groups —$SO_2$—$R_5$ and —S—$SO_2$—$R_5$, $R_5$ is an optionally substituted, especially aliphatic, cycloaliphatic, araliphatic or aromatic hydrocarbon radical with up to 18, preferably up to 10, carbon atoms. Examples of suitable groups $R_5$ are optionally substituted, such as lower alkoxy-, such as methoxy-, halogen-, such as fluorine-, chlorine- or bromine-, aryl-, such as phenyl-, and aryloxy- such as phenoxy-, monosubstituted or -polysubstituted alkyl groups, especially lower alkyl groups, such as methyl, ethyl or butyl groups, alkenyl groups, such as allyl or butenyl groups, cycloalkyl groups, such as cyclopentyl or cyclohexyl groups, or naphthyl or, especially, phenyl groups which are optionally monosubstituted or polysubstituted by lower alkyl, such as methyl, lower alkoxy, such as methoxy, halogen, such as fluorine, chlorine or bromine, aryl, such as phenyl, aryloxy, such as phenoxy, or nitro, for example phenyl, o-, m- or, preferably, p-tolyl, o-, m- or, preferably, p-methoxyphenyl, o-, m- or p-chlorophenyl, p-biphenylyl, p-phenoxyphenyl, p-nitrophenyl or 1- or 2-naphthyl.

In a starting material of the formula II, $R_2^A$ preferably represents an etherified hydroxyl group which, with the —C(=O)— grouping, forms an esterified carbonyl group which can be split, especially under mild conditions, it being possible for any functional groups which may be present in a carboxyl protective group $R_2^A$ to be protected in a manner which is in itself known, for example as indicated above. A group $R_2^A$ is, for example, in particular an optionally halogen-substituted lower alkoxy group, such as methoxy, α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy or 2-iodoethoxy, or an optionally substituted 1-phenyl-lower alkoxy group, such as a 1-phenyl-lower alkoxy group containing lower alkoxy, for example methoxy, or nitro, such as benzyloxy or diphenylmethoxy which is optionally, substituted, for example as indicated, for example benzyloxy, 4-methoxybenzyloxy, 4-nitrobenzyloxy, diphenylmethoxy or 4,4'-dimethoxy-diphenylmethoxy, and also an organic silyloxy or stannyloxy group, such as tri-lower alkylsilyloxy, for example trimethylsilyloxy, or halogen, for example chlorine. Preferably, in a starting material of the formula II, the radical $R_1^a$ denotes an amino protective group $R_1^A$, such as an acyl group Ac, wherein any free functional groups which may be present, for example amino, hydroxyl, carboxyl or phosphene groups, can be protected in a manner which is in itself known, amino groups, for example, by the abovementioned acyl, trityl, silyl or stannyl radicals, as well as substituted thio or sulphonyl radicals, and hydroxyl, carboxyl or phosphono groups, for example, by the abovementioned ether or ester groups, including silyl or stannyl groups, and $R_1^b$ denotes hydrogen.

In a secondary amino group —N($R_4^a$)($R_4^b$), one of the substituents $R_4^a$ and $R_4^b$ denotes hydrogen and the other denotes an aliphatic or cycloaliphatic hydrocarbon radical which contains up to 18, especially up to 12 and preferably up to 7, carbon atoms. Aliphatic hydrocarbon radicals $R_4^a$ or $R_4^b$ are, for example, optionally substituted alkyl groups, especially lower alkyl groups, for example alkyl groups, especially lower alkyl groups, substituted by lower alkoxy, such as methoxy, lower alkylthio, such as methylthio, cycloalkyl, such as cyclohexyl, aryl, such as phenyl, or heterocyclyl, such as thienyl, for example methyl, ethyl, propyl, isopropyl, butyl, isobutyl, pentyl, hexyl, 2-ethoxyethyl, 2-methylthioethyl, cyclohexylmethyl, benzyl or thienylmethyl. Cycloaliphatic hydrocarbon radicals $R_4^a$ or $R_4^b$ are, for example, optionally substituted cycloalkyl groups, for example cycloalkyl groups substituted by lower alkyl, such as methyl, lower alkoxy, such as methoxy, lower alkylthio, such as methylthio, cycloalkyl, such as cyclohexyl, aryl, such as phenyl, or heterocyclyl, such as furyl, such as cyclopropyl, cyclopentyl, cyclohexyl or cycloheptyl which are optionally substituted as indicated.

In tertiary amino groups —N($R_4^a$)($R_4^b$), each of the substituents $R_4^a$ and $R_4^b$ denotes one of the indicated aliphatic or cycloaliphatic hydrocarbon radicals, and $R_4^a$ and $R_4^b$ can be identical or different and the two substituents $R_4^a$ and $R_4^b$ can be linked together by a carbon-carbon bond or via an oxygen or sulphur atom or via an optionally substituted, such as lower alkylated, for example methylated, nitrogen atom.

Suitable tertiary amino groups N($R_4^a$)($R_4^b$) are, for example, dimethylamino, diethylamino, N-methylethylamino, diisopropylamino, N-methyl-isopropylamino, dibutylamino, N-methyl-isobutylamino, dicyclopropylamino, N-methyl-cyclopropylamino, dicyclopentylamino, N-methyl-cyclopentylamino, dicyclohexylamino, N-methyl-cyclohexylamino, dibenzylamino, N-methyl-benzylamino, N-cyclopropyl-benzylamino, 1-aziridinyl, 1-pyrrolidinyl, 1-piperidyl, 1H-2,3,4,5,6,7-hexahydroazepinyl, 4-morpholinyl, 4-thiomorpholinyl, 1-piperazinyl or 4-methyl-1-piperazinyl.

The cyclisation reaction, according to the invention, of a compound of the formula II to give a compound of the formula III is carried out in a suitable inert solvent, for example in an aliphatic, cycloaliphatic or aromatic hydrocarbon, such as hexane, cyclohexane, benzene or toluene, a halogenated hydrocarbon, such as methylene chloride, an ether, such as a di-lower alkyl ether, for example diethyl ether, a di-lower alkoxy-lower alkane, such as dimethoxyethane, a cyclic ether, such as dioxane or tetrahydrofurane, or an aliphatic, cycloaliphatic or aromatic nitrile, such as acetonitrile, or in a mixture thereof, optionally in the presence of an agent which absorbs moisture, for example a dried molecular sieve, at room temperature or with warming to about 150° C., preferably to about 80° to about 100° C., and if desired in an inert gas atmosphere, such as a nitrogen atmosphere.

The enamine of the formula III, which is formed by the cyclisation reaction, can be isolated, optionally as the crude product, or can be solvolysed in the same reaction solution to give a compound of the formula IA or IB. The double bond in the enamine of the formula III, which is formed as the intermediate product, can be in the 2,3-position or in the 3,4-position. A mixture of the two isomers can also be obtained. The resulting crude product can also already contain some solvolysis product of the formula IA or IB if water or alcohols of the formula $R_3$—OH are not completely excluded during the cyclisation reaction. The solvolysis can be prevented by working in the presence of agents which absorb moisture, such as dry molecular sieves. The compounds of the formula IA or IB can be obtained direct by carrying out the cyclisation reaction in the presence of a compound $R_3$—OH, especially a lower alkanol.

The solvolysis of resulting enamines of the formula III is carried out by adding water or an alcohol of the formula $R_3$—OH and if appropriate a catalytic to equimolar amount of an organic or inorganic acid, for example of a carboxylic, sulphonic or mineral acid, such as formic acid, acetic acid, benzenesulphonic acid, methanesulphonic acid, p-toluenesulphonic acid, hydrochloric acid, sulphuric acid or phosphoric acid, at temperatures of about $-10°$ C. to about 40° C., preferably at room temperature.

In the cyclisation and solvolysis reaction according to the invention it is possible, depending on the starting material and the reaction conditions, to obtain single compounds of the formula IA or IB or mixtures of compounds of the formula IA and IB. Resulting mixtures can be separated in a manner which is in itself known, for example with the aid of suitable methods of separation, for example by adsorption and fractional elution, including chromatography (column, paper or plate chromatography) using suitable adsorbents, such as silica gel or aluminium oxide, and eluants, and also by fractional crystallisation, solvent partition and the like.

Resulting compounds of the formulae IA and IB, which are suitable intermediates for the manufacture of pharmacologically more active end products, can be converted into such active end products by various additional measures which are in themselves known.

In a compound of the formulae IA or IB, obtained according to the invention, an α-phenyl-lower alkyl group $R_3$ can easily be split off and replaced by hydrogen. An optionally substituted α-phenyl-lower alkyl group, for example a benzyl or diphenylmethyl group, is split off, for example, by acidolysis, for example by treatment with a suitable inorganic or organic acid, such as hydrochloric acid, sulphuric acid, formic acid or especially trifluoroacetic acid, or by hydrogenolysis, for example by treatment with hydrogen in the presence of a catalyst, such as palladium. The resulting 3-hydroxy compounds are mainly in the 3-cephem form. The elimination of an α-phenyl-lower alkyl group $R_3$ can optionally be carried out selectively, that is to say without a carboxyl protective group $R_2^A$ being split off at the same time.

Enol-ethers, that is to say compounds of the formula LA and/or IB, wherein $R_3$ represents lower alkyl, are obtained from compounds of the formulae IA or IB, wherein $R_3$ is hydrogen or a radical which protects hydroxyl groups, and in the latter case are obtained by replacing this radical by hydrogen and subsequently etherifying the free hydroxyl group according to any process suitable for the etherification of enol groups. Preferably, the etherifying reagent used is a diazo compound of the formula $R_3-N_2$ corresponding to the radical $R_3$, above all an optionally substituted diazo-lower alkane, for example diazomethane, diazoethane or diazo-n-butane, or an optionally substituted α-phenyl-diazo-lower alkane, for example phenyl- or diphenyl-diazomethane. These reagents are used in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, a lower alkanol, for example methanol, ethanol or tert.-butanol, or an ether, such as a di-lower alkyl ether, for example diethyl ether, or a cyclic ether, for example tetrahydrofurane or dioxane, or of a solvent mixture and, depending on the diazo reagent, with cooling, at room temperature or with slight warming, and also, if necessary, in a closed vessel and/or under an inert gas atmosphere, for example a nitrogen atmosphere.

Furthermore, enol-ethers of the Formula IA and/or IB can be formed by treatment with a reactive ester of an alcohol of the formula $R_3-OH$ which corresponds to the lower alkyl radical or to the optionally substituted α-phenyl-lower alkyl radical, for example the benzyl or diphenylmethyl radical, $R_3$. Suitable esters are, above all, those with strong inorganic or organic acids, such as mineral acids, for example hydrogen halide acids, such as hydrochloric acid, hydrobromic acid or hydriodic acid, and also sulphuric acid or halogeno-sulphuric acids, for example fluorosulphuric acid, or strong organic sulphonic acids, such as lower alkanesulphonic acids which are optionally substituted, for example by halogen, such as fluorine, or aromatic sulphonic acids, such as, for example, benzenesulphonic acids which are optionally substituted, for example by lower alkyl, such as methyl, halogen, such as bromine, and/or nitro, for example methanesulphonic acid, trifluoromethanesulphonic acid or p-toluenesulphonic acid. These reagents, especially di-lower alkyl sulphates, such as dimethyl sulphate, and also lower alkyl fluorosulphates, for example methyl fluorosulphate, or optionally halogen-substituted methanesulphonic acid lower alkyl esters, for example trifluoromethanesulphonic acid methyl ester, are customarily used in the presence of a solvent, such as an optionally halogenated, such as chlorinated, aliphatic, cycloaliphatic or aromatic hydrocarbon, for example methylene chloride, an ether, such as dioxane or tetrahydrofuran, or a lower alkanol, such as methanol, or of a mixture. At the same time, suitable condensing agents are preferably employed, such as alkali metal carbonates or bicarbonates, for example sodium carbonate or bicarbonate or potassium carbonate or bicarbonate (usually together with a sulphate) or, organic bases, such as usually sterically hindered tri-lower alkylamines, for example N,N-di-isopropyl-N-ethylamine (preferably together with lower alkyl halogenosulphates or optionally halogen-substituted methanesulphonic acid lower alkyl esters), the reaction being carried out with cooling, at room temperature or with warming, for example at temperatures from about $-20°$ C. to about $50°$ C. and, if necessary, in a closed vessel and/or in an inert gas atmosphere, for example a nitrogen atmosphere.

The etherification reaction can be accelerated considerably by phase transfer catalysis. Phase transfer catalysts which can be used are quaternary phosphonium salts and, in particular, quaternary ammonium salts, such as optionally substituted tetraalkylammonium halides, for example tetrabutylammonium chloride, bromide or iodide, or also benzyl-triethylammonium chloride, in catalytic or up to equimolar amounts. Any of the solvents which are immiscible with water can serve as the organic phase, for example one of the optionally halogenated, such as chlorinated, aliphatic, cycloaliphatic or aromatic hydrocarbons, such as tri- or tetra-chloroethylene, di-, tri- or tetra-chloroethane, chlorobenzene or, in particular, carbon tetrachloride, or toluene or xylene. The alkali metal carbonates or bicarbonates, for example potassium carbonate or bicarbonate or sodium carbonate or bicarbonate, alkali metal phosphates, for example potassium phosphate, and alkali metal hydroxides, for example sodium hydroxide, which are suitable as condensing agents, can, in the case of base-sensitive compounds, be titrated into the reaction mixture so that the pH value remains approximately between 7 and 8.5 during the etherification.

Enol-ethers can also be manufactured by treatment with a compound which contains two or three etherified hydroxyl groups of the formula $R_3-O-$ on the same carbon atom of aliphatic character, that is to say with a corresponding acetol or ortho-ester, in the presence of an acid agent. Thus, for example, it is possible to use, as etherifying agents, gem-lower alkoxy-lower alkanes, such as 2,2-dimethoxypropane, in the presence of a strong organic sulphonic acid, such as p-toluenesulphonic acid, and of a suitable solvent, such as of a lower alkanol, for example methanol, or of a di-lower alkylsulphoxide or lower alkylenesulphoxide, for example dimethylsulphoxide, or ortho-formic acid tri-lower alkyl esters, for example ortho-formic acid triethyl ester, in the presence of a strong mineral acid, for example sulphuric acid, or of a strong organic sulphonic acid, such as p-toluenesulphonic acid, and of a suitable solvent, such as of a lower alkanol, for example ethanol, or of an ether, for example dioxane, and thus to obtain compounds of the formula IA and/or IB, wherein $R_3$ represents lower alkyl, for example methyl or ethyl.

The enol-ethers of the formula IA and/or IB can also be obtained when compounds of the formula IA and/or IB wherein $R_3$ denotes hydrogen and treated with tri-$R_3$-oxonium salts of the formula $(R_3)_3O^{\oplus}A^{\ominus}$ (so-called Meerwein salts), as well as di-$R_3$-O-carbenium salts of the formula $(R_3O)_2CH^{\oplus}A^{\ominus}$ or di-$R_3$-halonium salts of the formula $(R_3)_2Hal^{\oplus}A^{\ominus}$, wherein $A^{\ominus}$ denotes the anion of an acid and $Hal^{\oplus}$ denotes a halonium ion, especially a bromonium ion. The salts concerned are, above all, tri-lower alkyloxonium salts, as well as di-lower alkoxycarbenium salts or di-lower alkylhalonium salts, especially the corresponding salts with complex, fluorine-containing acids, such as the corresponding tetrafluoborates, hexafluophosphates, hexafluoantimonates or hexachloroantimonates. Such reagents are, for example, trimethyloxonium hexafluoantimonate, hexachloroantimonate, hexafluophosphate or tetrafluoborate or triethyloxonium hexafluoantimonate, hexachloroantimonate, hexafluophosphate or tetrafluoborate, dimethoxycarbenium hexafluophosphate or dimethylbromonium hexafluoantimonate. These etherifying agents are preferably used in an inert solvent, such as an ether or a halogenated hydrocarbon, for example diethyl ether, tetrahydrofurane or methylene chloride, or in a mixture thereof, if necessary in the presence of a base, such as an organic base, for example a preferably sterically hindered tri-lower alkylamine, for example, N,N-diisopropyl-N-ethylamine, and with cooling, at room temperature or with slight warming, for example at about $-20°$ C. to about $50°$ C., if necessary in a closed vessel and/or in an inert gas atmosphere, for example a nitrogen atmosphere.

The enol-ethers of the formulae IA and/or IB can also be manufactured by treating compounds of the formula IA and/or IB wherein $R_3$ denotes hydrogen with a 3-substituted 1-$R_3$-triazone compound (that is to say a compound of the formula Subst.—N=N—N-H—$R_3$), the substituent on the 3-nitrogen atom denoting an organic radical which is bonded via a carbon atom, preferably a carbocyclic aryl radical, such as an optionally substituted phenyl radical, for example lower alkylphenyl, such as 4-methylphenyl. Such triazine compounds are 3-aryl-1-lower alkyl-triazines, for example 3-(4-methylphenyl)-1-methyl-triazine, 3-(4-methylphenyl)-1-ethyl-triazine, 3-(4-methylphenyl)-1-n-propyl-triazine or 3-(4-methylphenyl)-1-isopropyl-triazene, and also 3-aryl-1-(α-phenyl-lower alkyl)triazenes, for example 1-benzyl-3-(4-methylphenyl)-triazine. These reagents are customarily used in the presence of inert solvents, such as optionally halogenated hydrocarbons or ethers, for example benzene, or solvent mixtures, and with cooling, at room temperature or preferably at elevated temperature, for example at about $20°$ C. to about $100°$ C., if necessary in a closed vessel and/or in an inert gas atmosphere, for example a nitrogen atmosphere.

The enol-ethers of the formula A and/or IB can also be obtained by reacting a compound of the formula IA and/or IB wherein —$OR_3$ is a reactive, esterified hydroxyl group with an alcohol of the formula $R_3$—OH wherein $R_3$ represents lower alkyl or α-phenyl-lower alkyl. Reactive esterified hydroxyl groups —$OR_3$ are, in particular, hydroxyl groups which are esterified with strong inorganic or organic acids, such as mineral acids, for example hydrogen halide acids, such as hydrochloric acid, hydrobromic acid or hydriodic acid, and also sulphuric acid or halogeno-sulphuric acids, for example fluorosulphuric acid, or, preferably, strong organic sulphonic acids, for example those of the formula HO—$SO_2$—$R_5$, wherein $R_5$ has the meaning indicated for $R_5$ further below under Y, such as lower alkanesulphonic acids which are optionally substituted, for example by halogen, such as fluorine, or aromatic sulphonic acids, for example benzenesulphonic acids which are optionally substituted, for example by lower alkyl, such as methyl, halogen, such as bromine, and/or nitro, for example especially methanesulphonic acid, trifluoromethanesulphonic acid or p-toluenesulphonic acid. The reaction with the alcohol $R_3OH$ is usually carried out in a solvent, such as an optionally halogenated, such as chlorinated, aliphatic, cycloaliphatic or aromatic hydrocarbon, for example benzene, toluene or methylene chloride, an ether, such as dioxane or tetrahydrofurane, a di-lower alkylamide, such as dimethylformamide or dimethylsulphoxide and the like, or in a mixture thereof, preferably in the presence of a suitable condensing agent, such as of an alkali metal carbonate or bicarbonate, for example sodium carbonate or bicarbonate or potassium carbonate or bicarbonate, or of an organic base, such as usually a sterically hindered tri-lower alkylamine, for example triethylamine or N,N-diisopropyl-N-ethylamine, the reaction being carried out with cooling, at room temperature or with warming, for example at temperatures from about $-20°$ C. to about $50°$ C. and, if necessary, in a closed vessel and/or in an inert gas atmosphere, for example in a nitrogen atmosphere.

Compounds of the formula IA and/or IB in which —$OR_3$ denotes a reactive esterified hydroxyl group are already known from German Offenlegungsschriften 2,408,686 and 2,408,698, or can be manufactured analogously to the methods described there from compounds, obtainable according to the invention, of the formula IA and/or IB wherein —$OR_3$ is a free hydroxyl group.

For example, sulphonic acid esters of compounds of the formula IA and/or IB, wherein $R_3$ denotes a —$SO_2$—$R_5$ group, can be manufactured by esterifying a compound of the formula IA and/or IB, wherein —$OR_3$ is a free hydroxyl group, with a reactive functional derivative of a sulphonic acid of the formula HO—$SO_2$—$R_5$.

Reactive functional derivatives of a sulphonic acid of the formula HO—$SO_2$—$R_5$ which are used are, for example, the reactive anhydrides thereof, especially the mixed anhydrides with hydrogen halide acids, for example the chlorides thereof, such as mesyl chloride and p-toluenesulphonic acid chloride.

The esterification is carried out, preferably in the presence of an organic tertiary nitrogen base, such as pyridine, triethylamine or ethyl-diisopropylamine, in a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofurane or dioxane, or a solvent mixture, and, depending on the reactivity of the esterifying reagent, with cooling, at room temperature or with slight warming, that is to say at temperatures from about $-10°$ C. to about $+50°$ C., and also, if necessary, in a closed vessel and/or under an inert gas atmosphere, for example a nitrogen atmosphere.

The resulting sulphonic acid ester can either be isolated or can be further processed in the same reaction mixture.

In the process according to the invention, and in additional measures which may require to be carried out, it is possible, if necessary, temporarily to protect, in a manner which is in itself known, free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation, and in each case to liberate them after the reaction has taken place, if desired, individually or conjointly, in a manner which is in itself known. Thus it is preferably possible, for example, to protect amino, hydroxyl, carboxyl or phosphono groups in an acyl radical $R_1^A$ or $R_1^b$, for example in the form of acylamino groups, such as those mentioned above, for example 2,2,2-trichloroethoxycarbonylamino, 2-bromoethoxycarbonylamino, 4-methoxybenzyloxycarbonylamino, diphenylmethoxycarbonylamino or tert.-butoxycarbonylamino groups, of arylthioamino or aryl-lower alkylthioamino groups, for example 2-nitrophenylthioamino groups or arylsulphonylamino groups, for example 4-methylphenylsulphonylamino groups, or of 1-lower alkoxycarbonyl-2-propylideneamino groups, or, respectively, of acyloxy groups, such as those mentioned above, for example tert.-butoxycarbonyloxy, 2,2,2-trichloroethoxycarbonyloxy or 2-bromoethoxycarbonyloxy groups, or, respectively, of esterified carboxyl groups, such as those mentioned above, for example diphenylmethoxycarbonyl groups, or, respectively, O,O'-disubstituted phosphono groups, such as those mentioned above, for example O,O'-di-lower alkylphosphono groups, for example O,O'-dimethylphosphono groups, and subsequently, if appropriate after conversion of the protective group, for example of a 2-bromoethoxycarbonyl group into a 2-iodoethoxycarbonyl group, if desired, to split the protected group, for example partially, in a manner which is in itself known and which depends on the nature of the protective group, for example a 2,2,2-trichloroethoxycarbonylamino or 2-iodoethoxycarbonylamino group by treatment with suitable reducing agents, such as zinc in the presence of aqueous acetic acid, a diphenylmethoxycarbonylamino or tert.-butoxycarbonylamino group by treatment with formic acid or trifluoroacetic acid, an arylthioamino or aryl-lower alkylthioamine group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, or a tert.-butoxycarbonyloxy group by treatment with formic acid or trifluoroacetic acid, or a 2,2,2-trichloroethoxycarbonyloxy group by treatment with a chemical reducing agent, such as zinc in the presence of aqueous acetic acid, or a diphenylmethoxycarbonyl group by treatment with formic acid or trifluoroacetic acid or by hydrogenolysis, or a O,O'-disubstituted phosphono group by treatment with an alkali metal halide.

In a compound of the formula IA or IB which is obtainable according to the invention and has a protected, especially an esterified, carboxyl group of the formula $-C(=O)-R_2^A$, the latter can be converted into the free carboxyl group in a manner which is in itself known, for example in accordance with the nature of the group $R_2^A$. An esterified carboxyl group, for example a carboxyl group esterified by a lower alkyl radical, especially methyl or ethyl, or by a benzyl radical, especially in a 2-cephem compound of the formula IB, can be converted into a free carboxyl group by hydrolysis in a weakly basic medium, for example by treatment with an aqueous solution of an alkali metal hydroxide or carbonate or an alkaline earth metal hydroxide or carbonate, for example sodium hydroxide or potassium hydroxide, preferably at a pH value of about 9 to 10, and optionally in the presence of a lower alkanol. A carboxyl group esterified by a suitable 2-halogeno-lower alkyl group or an arylcarbonylmethyl group can be split, for example by treatment with a chemical reducing agent, such as a metal, for example zinc, or a reducing metal salt, such as a chromium-II salt, for example chromium-II chloride, usually in the presence of a hydrogen donor, which, together with the metal, is able to produce nascent hydrogen, such as an acid, above all acetic acid, as well as formic acid, or of an alcohol, water preferably being added, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl grouping can be split, for example, by irradiation, preferably with ultraviolet light, for example below 290 mu when the arylmethyl group represents, for example, a benzyl radical which is optionally substituted in the 3-, 4- and/or 5-position, for example by lower alkoxy and/or nitro groups, or with ultraviolet light of longer wavelength, for example above 290 mu, when the arylmethyl group denotes, for example, a benzyl radical which is substituted in the 2-position by a nitro group, a carboxyl group esterified by a suitably substituted methyl group, such as tert.-butyl or diphenylmethyl, can be split, for example, by treatment with a suitable acid agent, such as formic acid or trifluoroacetic acid, optionally with the addition of a nucleophilic compound, such as phenol or anisole, an activated esterified carboxyl group, and also a carboxyl group present in the form of an anhydride, can be split by hydrolysis, for example by treatment with an acid or weakly basic aqueous agent, such as hydrochloric acid or aqueous sodium bicarbonate or an aqueous potassium-phosphate buffer with a pH of about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the customary manner, for example by treatment with water or an alcohol.

Resulting compounds of the formula IA or IB can be converted in a manner which is in itself known into other compounds of the formula IA or IB.

In a resulting compound it is possible, for example, to split off an amino protective group $R_1^A$ or $R_1^b$, especially an acyl group which can be split off easily, in a manner which is in itself known, for example to split off an α-polybranched lower alkoxycarbonyl group, such as tert.-butoxycarbonyl, by treatment with trifluoroacetic acid and a 2-halogeno-lower alkoxycarbonyl group, such as 2,2,2-trichloroethoxycarbonyl or 2-iodoethoxycarbonyl, or a phenacyloxycarbonyl group by treatment with a suitable reducing metal or a corresponding metal compound, for example zinc or a chromium-II compound, such as chromium-II chloride or chromium-II acetate, advantageously in the presence of an agent which, together with the metal or the metal compound, generates nascent hydrogen, preferably in the presence of aqueous acetic acid.

Furthermore, it is possible, in resulting compound of the formula IA or IB, wherein a carboxyl group of the formula —C(=O)—R$_2$ preferably represents a carboxyl group which is protected, for example by esterification, including by silylation, for exmple by reaction with a suitable organic halogenosilicon or halogeno-tin-IV compound, such as trimethylchlorosilane or tri-n-butyl-tin chloride, to split off an acyl group R$_1{}^a$ or R$_1{}^b$, wherein any free functional groups which may be present are optionally protected, by treatment with an imide-halide-forming agent, reaction of the resulting imide-halide with an alcohol and splitting of the iminoether formed, it being possible for a protected carboxyl group, for example a carboxyl group protected by an organic silyl radical, already to be liberated in the course of the reaction.

Imide-halide-forming agents in which halogen is bonded to an electrophilic central atom are, above all, acid halides, such as acid bromides and especially acid chlorides. The acid halides are, above all, acid halides of inorganic acids, above all of phosphorus-containing acids, such as phosphorus oxyhalides, phosphorus trihalides and especially phosphorus pentahalides, for example phosphorus oxychloride, phosphorus trichloride and, above all, phosphorus pentachloride, and also pyrocatechol-phosphorus trichloride, as well as acid halides, especially acid chlorides, of sulphur-containing acids or of carboxylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monoamine or diamine, such as a tri-lower alkylamine, for example trimethylamine, triethylamine or N,N-diisopropyl-N-ethylamine, and also of a N,N,N',N'-tetra-lower alkyl-lower alkylenediamine, for example N,N,N',N'-tetramethyl-1,5-pentylenediamine or N,N,N',N'-tetramethyl-1,6-hexylenediamine, of a monocyclic or bicyclic monoamine or diamine, such as of a N-substituted, for example N-lower alkylated, alkyleneamine, azealkyleneamine or oxaalkyleneamine, for example N-methylpiperidine or N-methylmorpholine, and also 2,3,4,6,7,8-hexahydro-pyrrolo[1,2-a]pyrimidine (diazabicyclononene; DBN), or of a tertiary aromatic amine, such as a di-lower alkyl-aniline, for example N,N-dimethylaniline, or, above all, of a tertiary heterocyclic, monocyclic or bicyclic base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; however, the latter can also be present in more than or less than the equimolar amount, for example in an about 0.2-fold to about 1-fold amount or in an approximately up to 10-fold, especially an approximately 3-fold to 5-fold, excess.

The reaction with the imide-halide-forming agent is preferably carried out with cooling, for example at temperatures from about −50° C. to about +10° C., but it is also possible to work at higher temperatures, that is to say, for example, up to about 75° C., if the stability of the starting materials and of the products permits an elevated temperature.

The imide-halide product, which is usually further processed without isolation, is reacted, according to the process, with an alcohol, preferably in the presence of one of the abovementioned bases, to give the imino-ether. Examples of suitable alcohols are aliphatic as well as araliphatic alcohols, above all optionally substituted, such as halogenated, for example chlorinated, lower alkanols or lower alkanols which contain additional hydroxyl groups, for example ethanol, propanol or butanol but especially methanol, and also 2-halogeno-lower alkanols, for example 2,2,2-trichloroethanol or 2-bromoethanol, as well as optionally substituted phenyl-lower alkanols, such as benzyl alcohol. Usually an excess, for example an up to about 100-fold excess, of the alcohol is used and the reaction is preferably carried out with cooling, for example at temperatures from about −50° C. to about 10° C.

The imino-ether product can advantageously be subjected to splitting without isolation. Splitting of the imino-ether can be achieved by treatment with a suitable hydroxy compound, preferably by means of hydrolysis, and also by alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5, which can, if necessary, be obtained by adding a basic agent, such as an aqueous alkali metal hydroxide, for example sodium hydroxide or potassium hydroxide, or an acid, for example a mineral acid or an organic acid, such as hydrochloric acid, sulphuric acid, phosphoric acid, fluoboric acid, trifluoroacetic acid or p-toluenesulphonic acid.

The three-stage process described above for splitting off an acyl group is advantageously carried out without isolation of the imide-halide an imino-ether intermediate products, usually in the presence of an organic solvent which is inert with respect to the reactants, such as an optionally halogenated hydrocarbon, for example methylene chloride, and/or in an inert gas atmosphere, such as a nitrogen atmosphere.

If the imide-halide intermediate product obtainable according to the above process is reacted, instead of with an alcohol, with a salt, such as an alkali metal salt of a carboxylic acid, especially of a sterically hindered carboxylic acid, a compound of the formula IA or IB, wherein both the radicals R$_1{}^a$ and R$_1{}^b$ represent acyl groups, is obtained.

In a compound of the formula IA or IB wherein both of the radicals R$_1{}^a$ and R$_1{}^b$ represent acyl groups, one of these groups, preferably the sterically less hindered group, can be removed selectively, for example by hydrolysis or aminolysis.

In a compound of the formulae IA or IB wherein R$_1{}^A$ and R$_1{}^b$, together with the nitrogen atom, represent a phthalimido group, the latter can be converted into the free amino group, for example by hydrazinolysis, that is to say on treatment of such a compound with hydrazine.

Certain acyl radicals R$_1{}^A$ of an acylamino grouping in compounds obtainable according to the invention, such as, for example, the 5-amino-5-carboxy-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl, or phthaloyl, can also be split off by treatment with a nitrosylating agent, such as nitrosyl chloride, with a carbocyclic arenediazonium salt, such as benzenediazonium chloride, or with an agent which releases positive halogen, such as a N-halogeno-amide or a N-halogeno-imide, for example N-bromosuccinimide, preferably in a suitable solvent or solvent mixture, such as formic acid, together with a nitro-lower alkane or cyano-lower alkane, and treatment of the reaction product with a hydroxylic agent, such as water or a lower alkanol, for example methanol, or, if, in the 5-amino-5-carboxy-valeryl radical $R_1^A$, the amino group is substituted and the carboxyl group is protected, for example by esterification, and $R_1^b$ preferably represents an acyl radical but can also denote hydrogen, by leaving the substance to stand in an inert solvent, such as dioxane or a halogenated aliphatic hydrocarbon, for example methylene chloride, and, if necessary, working up the free or mono-acylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group $R_1^A$, such as the trityl group $R_1^A$, can be split off, for example, by treatment with an acid agent, such as a mineral acid, for example hydrochloric acid.

In a compound of the formula IA or IB, wherein $R_1^a$ and $R_1^b$ represent hydrogen, the free amino group can be substituted according to methods which are in themselves known, above all acylated by treatment with acids, such as a carboxylic acid, or reactive derivatives thereof.

If a free acid in which any functional groups which may be present, such as an amino group which may be present, are preferably protected, is employed for the acylation, suitable condensing agents are customarily used, such as carbodiimides, for example N,N'-diethyl-, N,N'-dipropyl-, N,N'-diisopropyl, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenyl-isoxazolinium 3'-sulphonate and N-tert.-butyl-5-methyl-isoxazolinium perchlorate, or a suitable acylamino compound, for example 2-ethoxy-1-ethoxycarbonyl-1,2-dihydroquinoline.

The condensation reaction is preferably carried out in one of the anhydrous reaction media mentioned further below, for example in methylene chloride, dimethylformamide or acetonitrile.

An amide-forming functional derivative of an acid, in which groups which may be present, such as an amino group which may be present, are preferably protected, is above all an anhydride of such an acid, including, and preferably, a mixed anhydride. Mixed anhydrides are, for example, those with inorganic acids, especially with hydrogen halide acids, that is to say the corresponding acid halides, for example acid chlorides or acid bromides, and also with hydrazoic acid, that is to say the corresponding acid azides, with a phosphorus-containing acid, for example phosphoric acid or phosphorous acid, with a sulphur-containing acid, for example sulphuric acid, or with hydrocyanic acid. Further mixed anhydrides are, for example, those with organic acids, such as organic carboxylic acids, such as with lower alkane-carboxylic acids which are optionally substituted, for example by halogen, such as fluorine or chlorine, for example pivalic acid or trichloroacetic acid, or with half-esters, especially lower alkyl half-esters, of carbonic acid, such as the ethyl or isobutyl half-ester of carbonic acid, or with organic, especially aliphatic or aromatic, sulphonic acids, for example p-toluenesulphonic acid.

It is also possible to use, as acylating agents, inner anhydrides, such as ketenes, for example diketene, isocyanates, (that is to say inner anhydrides of carbamic acid compounds) or inner anhydrides of carboxylic acid compounds having carboxyl-substituted hydroxyl or amino groups, such as mandelic acid O-carboxanhydride or the anhydride of 1-N-carboxyaminocyclohexanecarboxylic acid.

Further acid derivatives which are suitable for reaction with the free amino group are activated esters, in which any functional groups which may be present are usually protected, such as esters with vinylogous alcohols (that is to say enols), such as vinylogous lower alkanols, or aryl esters, such as phenyl esters which are preferably substituted, for example by nitro or by halogen, such as chlorine, for example pentachlorophenyl, 4-nitrophenyl or 2,4-dinitrophenyl esters, heteroaromatic esters, such as benztriazole esters, or diacylimino esters, such as succinylimino esters or phthalylimino esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as a tri-lower alkylamine, for example triethylamine, a N,N-di-lower alkylaniline, for example N,N-dimethylaniline, or a base of the pyridine type, for example pyridine, of an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or of an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In the above N-acylation reactions it is possible to start from compounds of the formulae IA or IB, wherein $R_3$ is lower alkyl or an optionally substituted α-phenyl-lower alkyl group, for example a benzyl or diphenylmethyl group, and $R_2$ has the above meaning, and compounds having free carboxyl groups of the formula $-C(=O)-R_2$, wherein $R_2$ represents hydroxyl, can also be used in the form of salts, for example ammonium salts, such as with triethylamine, or in the form of a compound with a carboxyl group protected by reaction with a suitable organic phosphorus halide compound, such as with a lower alkyl-phosphorus dihalide or lower alkoxy-phosphorus dihalide, such as methyl-phosphorus dichloride, ethyl-phosphorus dibromide or methoxyl-phosphorus dichloride; in the resulting acylation product, the protected carboxyl group can be liberated in a manner which is in itself known, for example as described above, including by hydrolysis or alcoholysis.

An acyl group can also be introduced by acylating a compound of the formula IA or IB, wherein $R_1^a$ and $R_1^b$ together represent an ylidene radical (which can also be introduced subsequently, for example by treatment of a compound wherein $R_1^a$ and $R_1^b$ represent hydrogen with an aldehyde, such as an aliphatic, aromatic or araliphatic aldehyde), for example according to the methods indicated above, and the acylation product can be hydrolysed, preferably in a neutral or weakly acid medium.

An acyl group can also be introduced stepwise. Thus, for example, it is possible to introduce into a compound of the formula IA or IB, having a free amino group, a halogeno-lower alkanoyl group, for example a bromoacetyl group, or, for example by treatment with a carbonic acid dihalide, such as phosgene, a halogenocarbonyl group, for example a chlorocarbonyl group, and to react a H-(halogeno-lower alkanoyl)amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol, and thus to obtain substituted N-lower alkanoylamino or N-hydroxycarbonylamino compounds.

In both reactants, free functional groups can temporarily be protected during the acylation reaction, in a manner which is in itself known, and can be liberated, after the acylation, by means of methods which are in themselves known, for example as described above.

The acylation can also be effected by replacement of an already existing acyl group by another, preferably sterically hindered, acyl group, for example according to the process described above, by manufacturing the imide-halide compound, treating this with a salt of an acid and splitting off hydrolytically one of the acyl groups present in the product thus obtainable, usually the sterically less hindered acyl group.

It is furthermore possible, for example, to react a compound of the formula IA or IB, wherein $R_1^a$ represents a glycyl group which is preferably substituted in the α-position, such as phenylglycyl, and $R_1^b$ represents hydrogen, with an aldehyde, for example formaldehyde, or a ketone, such as a lower alkanone, for example acetone, and thus to obtain compounds of the formula IA or IB, wherein $R_1^A$ and $R_1^b$, together with the nitrogen atom, represent a 5-oxo-1,3-diaza-cyclopentyl radical which is preferably substituted in the 4-position and optionally substituted in the 2-position.

In a compound of the formula IA or IB, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkyl-silane, lower alkoxy-lower alkyl-dihalogenosilane or tri-lower alkyl-silyl halide, for example dichlorodimethylsilane, methoxy-methyl-dichloro-silane, trimethylsilyl chloride or dimethyl-tert.-butyl-silyl chloride, such silyl halide compounds preferably being used in the presence of a base, for example pyridine, or by treatment with an optionally N-mono-lower alkylated, N,N-di-lower alkylated, N-tri-loweralkyl)silylated or N-lower alkylated-N-(tri-lower alkyl)silylated N-(tri-lower alkylsilyl)-amine (see, for example, British Pat. No. 1,073,530), or with a silylated carboxylic acid amide, such as a bis-tri-lower alkylsilyl-acetamide, for example bis-tri-methyl-silyl-acetamide, or trifluorosilylacetamide, or by treatment with a suitable stannylating agent, such as a bis-(trilower alkyl-tin)oxide, for example bis-(tri-n-butyl-tin)oxide, a tri-lower alkyl-tin hydroxide, for example tri-ethyl-tin hydroxide, a tri-lower alkyl-lower alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification 67/11107).

In a compound of the formula IA or IB, obtainable according to the process, which contains a free carboxyl group of the formula $-C(=O)-R_2$, such a group can be converted into a protected carboxyl group in a manner which is in itself known. Thus esters are obtained, for example, by treatment with a suitable diazo compound, such as a diazo-lower alkane, for example diazomethane or diazobutane, or a phenyl-diazo-lower alkane, for example diphenyldiazomethane, if necessary in the presence of a Lewis acid, such as, for example, boron trifluoride, or by reaction with an alcohol suitable for the esterification reaction, in the presence of an esterifying agent, such as a carbodiimide, for example dicyclohexylcarbodiimide, as well as carbonyldiimidazole, and also with a N,N'-di-substituted O- or S-substituted isourea or isothiourea, wherein an O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the aid with a reactive ester of an alcohol and of a strong inorganic acid, or with a strong organic sulphonic acid. Furthermore, acid halides, such as acid chlorides (manufactured, for example, by treatment with oxalyl chloride), activated esters (formed, for example, with a N-hydroxy-nitrogen compound, such as N-hydroxy-succinimide) or mixed anhydrides (obtained, for example, with halogenoformic acid lower alkyl esters, such as chloroformic acid ethyl ester or chloroformic acid isobutylester, or with halogenoacetic acid halides, such as trichloroacetic acid chloride) can be converted into an esterified carboxyl group by reaction with alcohols, optionally in the presence of a base, such as pyridine.

In a resulting compound having an esterified grouping of the formula $-C(=O)-R_2$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be manufactured by reacting a compound of the formula IA or IB, having a free carboxyl group of the formula —C(=O)—R$_2$, preferably a salt, especially an alkali metal salt, for example a sodium salt, or an ammonium salt, for example a triethylammonium salt, thereof, with a reactive derivative, such as a halide, for example the chloride, of an acid, for example a halogenoformic acid lower alkyl ester or a lower alkanecarboxylic acid chloride.

In a compound, obtainable according to the process, which has a free carboxyl group of the formula —C(=O)—R$_2$, such a group can also be converted into an optionally substituted carbamoyl or hydrazinocarbonyl group, for which preferably reactive functionally modified derivatives, such as the abovementioned acid halides, and generally esters, such as also the abovementioned activated esters, or mixed anhydrides of the appropriate acid are reacted with ammonia or amines, including hydroxylamine, or hydrazines.

A carboxyl group protected by an organic silyl or stannyl group can be formed in a manner which is in itself known, for example by treating compounds of the formulae IA or IB, wherein R$_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17107.

It is furthermore possible to liberate modified functional substituents in groups $R_1^A$, $R_1^b$ and/or R$_2$, such as substituted amino groups, acylated hydroxyl groups, esterified carboxyl groups or O,O'-di-substituted phosphono groups, according to methods which are in themselves known, for example those described above, or functionally to modify free functional substituents in groups $R_1^A$, $R_1^b$ and/or R$_2$, such as free amino, hydroxyl, carboxyl or phosphono groups, according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanyl semicarbazide with sodium nitrite can be reacted with a compound of the formula IA or IB wherein, for example, the amino protective group $R_1^A$ represents an optionally substituted glycyl group, and the amino group can thus be converted into a 3-guanylureido group. Furthermore, compounds with aliphatically bonded halogen, for example with an optionally substituted α-bromoacetyl grouping, can be reacted with esters of phosphorous acid, such as tri-lower alkyl-phosphite compounds, and corresponding phosphono compounds can thus be obtained.

Resulting cephem compounds of the formula IA and IB can be converted into 1-oxides of the corresponding 3-cephem compounds of the formula IA by oxidation with suitable oxidising agents, such as those described below. Resulting 1-oxides of 3-cephem compounds of the formula IA can be reduced to the corresponding 3-cephem compounds of the formula IA by reduction with suitable reducing agents, such as, for example, those described below. In these reactions care must be taken to ensure that, if necessary, free functional groups are protected and, if desired, are subsequently liberated again.

Resulting cephem compounds can be isomerised. Thus, resulting 2-cephem compounds of the formula IB, or resulting mixtures of 2- and 3-cephem compounds, can be converted into the corresponding 3-cephem compounds of the formula IA by isomerising a 2-cephem compound of the formula IB, or a mixture consisting of a 2- and 3-cephem compound, wherein free functional groups can, if appropriate, temporarily be protected, for example as indicated. In this reaction it is possible to use, for example, 2-cephem compounds of the formula IB, wherein the group of the formula —C(=O)—R$_2$ represents a free or protected carboxyl group, it also being possible for a protected carboxyl group to be formed during the reaction.

Thus, it is possible to isomerise a 2-cephem compound of the formula IB by treating it with a basic agent and isolating the corresponding 3-cephem compound of the formula IA from an equilibrium mixture of the 2- and 3-cephem compounds which may be obtained.

Suitable isomerising agents are, for example, organic nitrogen-containing bases, such as tertiary heterocyclic bases of aromatic character, and above all tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methylpiperidine, or N-phenyl-lower alkyl-N,N-di-lower alkylamines, for example N-benzyl-N,N-dimethylamine, as well as mixtures thereof, such as the mixture of a base of the pyridine type, for example pyridine, and a N,N,N-tri-lower alkylamine, for example the mixture of pyridine and triethylamine. Furthermore, it is also possible to use inorganic or organic salts of bases, especially of medium strength to strong bases, with weak acids, such as alkali metal salts or ammonium salts of lower alkanecarboxylic acids, for example sodium acetate, triethylammonium acetate or N-methylpiperidine acetate, as well as other analogous bases or mixtures of such basic agents.

The above isomerisation with basic agents can be carried out, for example, in the presence of a derivative of a carboxylic acid which is suitable for forming a mixed anhydride, such as a carboxylic acid anhydride or carboxylic acid halide, for example with pyridine in the presence of acetic anhydride. The reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases which are used as reactants and are liquid under the reaction conditions at the same time also to serve as solvents, if necessary with cooling or heating, preferably in a temperature range from about −30° C. to about +100° C., in an inert gas atmosphere, for example a nitrogen atmosphere, and/or in a closed vessel.

The 3-cephem compounds of the formula IA, thus obtainable, can be separated from any 2-cephem compounds of the formula IB, which may still be present, in a manner which is in itself known, for example by adsorption and/or crystallisation.

The isomerisation of 2-cephem compounds of the formula IB can also be carried out by oxidising these in the 1-position, if desired separating an obtainable isomer mixture of the 1-oxides of 3-cephem compounds of the formula IA, and reducing the 1-oxides of the corresponding 3-cephem compounds of the formula IA, thus obtainable.

Suitable oxidising agents for the oxidation of 2-cephem compounds in the 1-position are inorganic per-acids which have a reduction potential of at least $+1.5$ volt and which consist of non-metallic elements, organic per-acids or mixtures of hydrogen peroxide and acids, especially organic carboxylic acids, with a dissociation constant of at least $10^{-5}$. Suitable inorgaic per-acids are periodic acid and persulphuric acid. Organic per-acids are appropriate percarboxylic acids and per-sulphonic acids which can be added as such or can be formed in situ by using at least one equivalent of hydrogen peroxide and of a carboxylic acid. It is appropriate to use a large excess of the carboxylic acid when, for example, acetic acid is used as the solvent. Suitable per-acids are, for example, performic acid, peracetic acid, pertrifluoroacetic acid, permaleic acid, perbenzoic acid, monoperphthalic acid or p-toluenepersulphonic acid.

The oxidation can also be carried out using hydrogen peroxide with catalytic amounts of an acid having a dissociation constant of at least $10^{-5}$ and it is possible to employ low concentrations, for example 1–2% and less, but also larger amounts, of the acid. The activity of the mixture depends, above all, on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Examples of acids which are suitable as catalysts are acetic acid, perchloric acid and trifluoroacetic acid. Usually at least equimolar amounts of the oxidising agent, and preferably a small excess of about 10% to about 20%, are used: the oxidation is carried out under mild conditions, for example at temperatures from about $-50°$ C. to about $+100°$ C., preferably from about $-10°$ C. to about $+40°$ C.

The oxidation of 2-cephem compounds to the 1-oxides of the corresponding 3-cephem compounds can also be carried out by treatment with ozone, as well as with organic hypohalite compounds, such as lower alkyl hypochlorites, for example tert.-butyl hypochlorite, which are used in the presence of inert solvents, such as optionally halogenated hydrocarbons, for example methylene chloride, and at temperatures of about $-10°$ C. to about $+30°$ C., with periodate compounds, such as alkali metal periodates, for example potassium periodate, which are preferably used in an aqueous medium at a pH value of about 6 and at temperatures of about $-10°$ C. to about $+30°$ C., with iodobenzene dichloride, which is used in an aqueous medium, preferably in the presence of an organic base, for example pyridine, and with cooling, for example at temperatures of about $-20°$ C. to about $0°$, or with any other oxidising agent which is suitable for conversion of a thio grouping into a sulphoxide grouping.

In the 1-oxides of 3-cephem compounds of the formula IA, thus obtainable, especially in those compounds in which $R_1^a$, $R_1^b$ and $R_2$ have the preferred meanings mentioned above, the groups $R_1^a$, $R_1^b$ and/or $R_2$ can, within the defined framework, be converted into one another, split off or introduced. A mixture of isomeric α- and β-1-oxides can be separated, for example chromatographically.

The reduction of the 1-oxides of 3-cephem compounds of the formula IA can be carried out in a manner which is in itself known by treatment with a reducing agent, if necessary in the presence of an activating agent. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of an inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediamine tetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinuous, phosphonous or phosphorous acid, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by one divalent organic radical or two monovalent organic radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which are above all employed together with the dithionite, iodide or ferrocyanide reducing agents and the trivalent phosphorus reducing agents which do not contain halogen, or in the catalytic reduction, there may be mentioned, in particular, organic carboxylic acid halides and sulphonic acid halides, as well as sulphur halides, phosphorus halides or silicon halides having the same or a greater second order hydrolysis constant than benzoyl chloride, for example phosgene, oxalyl chloride, acetic acid chloride or acetic acid bromide, chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane, and also suitable acid anhydrides, such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting materials and the choice of the reducing agent, and thus, for example, is carried out in the presence of lower alkanecarboxylic acids or esters thereof, such as acetic acid and ethyl acetate, in the case of the catalytic reduction and, for example, in the presence of optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide, dimethylacetamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone and the like, together with the chemical reducing agents, these solvents preferably not containing any water. The reaction is usually carried out at temperatures from about $-20°$ C. to about $100°$ C., it being possible for the reaction to be carried out at lower temperatures when very reactive activating agents are used.

In the 3-cephem compounds of the formula IA, thus obtainable, $R_1{}^a$, $R_1{}^b$ and/or $R_2$ can be converted into other groups $R_1{}^a$, $R_1{}^b$ or $R_2$, as described above.

Salts of compounds of the formulae IA and IB can be manufactured in a manner which is in itself known. Thus, salts of those compounds which possess acid groups can be formed, for example, by treatment with metal compounds, such as alkali metal salts of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formulae IA and IB which possess basic groupings are obtained in the customary manner, for example by treatment with an acid or a suitable anion exchange reagent. Inner salts of compounds of the formulae IA and IB, which contain a salt-forming amino group and a free carboxyl group, can be formed, for example, by neutralising salts, such as acid addition salts, to the isoelectric point, for example with weak bases, or by treatment with liquid ion exchangers. Salts of 1-oxides of compounds of the formula IA which possess salt-forming groups can be manufactured in an analogous manner.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation methods. Resulting racemates can be resolved into the antipodes in the customary manner, if appropriate after introducing suitable salt-forming groupings, for example by forming a mixture of diastereomeric salts with optically active salt-forming agents, separating the mixture into the diastereomeric salts and converting the salts into the free compounds, or by fractional crystallisation from optically active solvents.

The process also comprises those embodiments according to which compounds arising as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds mentioned initially as being particularly preferred are obtained.

In the starting compounds of the formula II, the leaving group Y is preferably a $-SO_2-R_5$ group, wherein $R_5$ has the indicated meaning, but especially the meaning indicated as being preferred.

The process according to the invention is distinguished, relative to previously known processes, by the fact that it starts from inexpensive, easily accessible starting materials, such as, in particular, the 1-oxides of the fermentatively obtainable penicillins G or V and of 6-amino-penicillanic acid, the reactive groups of which can be protected in any known manner and can easily be liberated again after the reaction, and that the manufacture of the intermediate products required according to the invention takes place with high yields. In particular, the process also permits the direct manufacture of compounds of the formula I wherein $R_3$ denotes hydrogen, without a hydroxyl protective group $R_3$ having to be split off.

The starting materials of the formula II, used according to the invention, can be manufactured, for example, in accordance with the following equation.

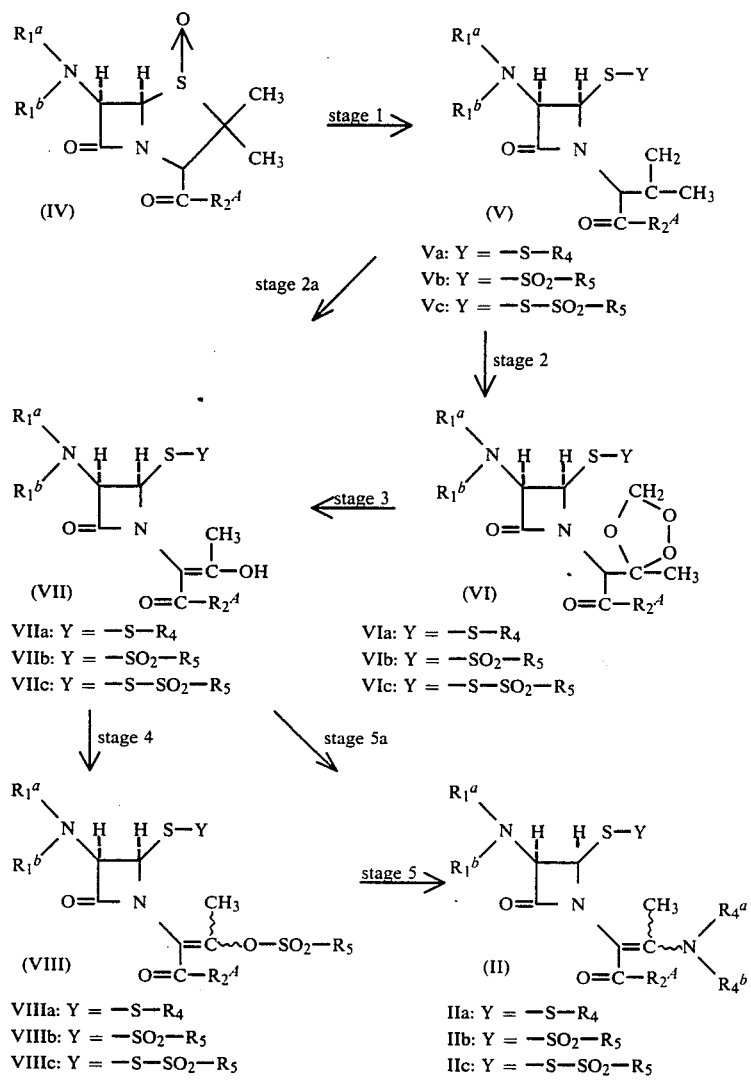

Starting compounds of the formula IV are known or can be manufactured according to known processes.

Compounds of the formula Va are also known or can be manufactured according to Netherlands Patent Specification 72/08671.

The new compounds of the formulae VIIIa, VIIIb, VIIIc, IIa, IIb and IIc, in which $R_1{}^a$, $R_1{}^b$, $R_2{}^A$ and Y have the meaning indicated under formula II, and also processes for their manufacture are also a subject of the present invention.

Compounds of the formula Vb can be obtained from compounds of the formula IV by reaction with a sulphinic acid of the formula $HSO_2$—$R_5$ or a sulphonyl cyanide of the formula $N\equiv C$—$SO_2$—$R_5$. Compounds of the formula IVc can be obtained from compounds of the formula IV by reaction with a thiosulphonic acid of the formula H—S—$SO_2$—$R_5$. The reaction is carried out in an inert solvent or solvent mixture, for example an optionally halogenated, such as chlorinated, aliphatic, cycloaliphatic or aromatic hydrocarbon, such as pentane, hexane, cyclohexane, benzene, toluene, methylene chloride, chloroform or chlorobenzene, an aliphatic, cycloaliphatic or aromatic alcohol, such as a lower alkanol, for example methanol or ethanol, cyclohexanol or phenol, a polyhydroxy compound, for example a polyhydroxyalkane, such as a dihydroxy-lower alkane, for example ethylene glycol or propylene glycol, a lower ketone, such as acetone or methyl ethyl ketone, an ether-like solvent, such as diethyl ether, dioxane or tetrahydrofurane, a lower carboxylic acid amide, such as dimethylformamide or dimethylacetamide, a lower dialkylsulphoxide, such as dimethylsulphoxide and the like or mixtures thereof.

The reaction is carried out at room temperature or preferably at elevated temperature, for example at the boiling point of the solvent employed, if desired in an inert gas atmosphere, such as a nitrogen atmosphere.

The reaction with the sulphonyl cyanide of the formula $N\equiv C$—$SO_2$—$R_5$ is accelerated by the addition of compounds which provide halogen anions. Examples of suitable compounds which provide halogen anions are quaternary ammonium halides, especially chlorides and bromides, such as tetra-lower alkylammonium halides which are optionally substituted at the lower alkyl groups, for example monosubstituted or polysubstituted by aryl, such as phenyl, such as tetraethylammonium chloride or bromide or benzyltriethylammonium chloride or bromide. The compounds which provide halogen anions are added in amounts of about 1 to about 50 mol percent, preferably of about 2 to about 5 mol percent.

Compounds of the formula Vb and Vc can also be obtained by reacting a compound of the formula IV with a heavy metal sulphinate of the formula $M^{n+}(^-SO_2-R_5)_n$ or with a heavy metal thiosulphonte of the formula $M^{n+}(^-S-SO_2-R_5)_n$, wherein M represents a heavy metal cation and n denotes the valency of this cation. Suitable heavy metal sulphinates or heavy metal thiosulphonates are in particular those which have a higher solubility product in the reaction medium used than the heavy metal compounds of the formula $M^{n+}(-S-R_4)_n$ which are formed during the reaction. Suitable heavy metal cations $M^{n+}$ are, in particular, those which form particularly sparingly soluble sulphides. These include, for example, the monovalent or divalent cations of copper, mercury, silver and tin, copper$^{++}$ and silver$^+$ cations being preferred.

The heavy metal sulphinate or heavy metal thiosulphonate can either be employed as such or can be formed in situ during the reaction, for example from a sulphinic acid of the formula $HSO_2-R_5$ or from a thiosulphonic acid of the formula $H-S-SO_2-R_5$ or from a soluble salt thereof, for example an alkali metal salt, such as a sodium salt, and a heavy metal salt, the solubility product of which is greater than that of the heavy metal sulphinate or heavy metal thiosulphonate formed, for example a heavy metal nitrate, acetate or sulphate, for example silver nitrate, mercury-II diacetate or copper-II sulphate, or a soluble chloride, such as tin-II chloride dihydrate.

The reaction of a compound of the formula Va with the heavy metal sulphinate of the formula $M^{n+}(^-SO_2-R_5)_n$ or the heavy metal thiosulphonate of the formula $M^{n+}(^-S-SO_2-R_5)_n$ can be carried out in an inert organic solvent, in water or in a solvent mixture consisting of water and a water-miscible solvent. Suitable inert organic solvents are, for example, aliphatic, cycloaliphatic or aromatic hydrocarbons, such as pentane, hexane, cyclohexane, benzene, toluene or xylene, or aliphatic, cycloaliphatic or aromatic alcohols, such as lower alkanols, for example methanol or ethanol, cyclohexanol or phenol, polyhydroxy compounds, such as polyhydroxyalkanes, for example dihydroxy-lower alkanes, such as ethylene glycol or propylene glycol, carboxylic acid esters, for example lower carboxylic acid lower alkyl esters, such as ethyl acetate, lower ketones, such as acetone or methyl ethyl ketone, etherlike solvents, such as dioxane or tetrahydrofurane or polyethers, such as dimethoxyethane, lower carboxylic acid amides, such as dimethylformamide, lower alkylnitriles, such as acetonitrile, or lower sulphoxides, such as dimethylsulphoxide. The reaction usually proceeds considerably more rapidly in water or especially in mixtures of water and one of the solvents mentioned, including emulsions, than in the organic solvents alone.

The reaction temperature is usually room temperature but can be lowered in order to slow down the reaction or raised, say up to the boiling point of the solvent employed, to accelerate the reaction, it being possible to carry out the reaction under normal pressure or elevated pressure.

In a resulting compound of the formula V, a group $R_1^a$, $R_1^b$ or $R_2^A$ can be converted into another group $R_1^a$, $R_1^b$ or $R_2^A$, for which purpose it is possible to use analogous reactions to those indicated for the conversion of these groups in the case of compounds of the formula IA or IB.

In stage 2 and 3 or 2a, a compound of the formula V can be converted into a compound of the formula VII by oxidative degradation of the methylene group to an oxo group.

The oxidative elimination of the methylene group in compounds of the formula V, with the formation of an oxo group, can be carried out by forming an ozonide compound of the formula VI by treatment with ozone. In this reaction, ozone is usually employed in the presence of a solvent, such as an alcohol, for example a lower alkanol, such as methanol or ethanol, a ketone, for example a lower alkanone, such as acetone, an optionally halogenated aliphatic, cycloaliphatic or aromatic hydrocarbon, for example a halogeno-lower alkane, such as methylene chloride or carbon tetrachloride, or of a solvent mixture, including an aqueous mixture, and with cooling or slight warming, for example at temperatures from about $-90°$ C. to about $+40°$ C.

An ozonide of the formula VIa, obtained as an intermediate product, can, optionally without isolation, be converted into a compound of the formula VIb or VIc by reaction with a heavy metal sulphinate of the formula $M^{n+}(^-SO-R^5)_n$ or, respectively, a heavy metal thiosulphonate of the formula $M^{n+}(^-S-SO_2-R_5)_n$, analogously to the conversion of compounds of the formula Va to compounds of the formula Vb and Vc respectively.

An ozonide of the formula V can be split by reduction in stage 3 to give a compound of the formula VII, for which reaction it is possible to use catalytically activated hydrogen, for example hydrogen in the presence of a heavy metal hydrogenation catalyst, such as a nickel catayst and also a palladium catalyst, preferably on a suitable carrier, such as calcium carbonate or charcoal, or chemical reducing agents, such as reducing heavy metals, including heavy metal alloys or heavy metal amalgams, for example zinc, in the presence of a hydrogen donor, such as an acid, for example acetic acid, or of an alcohol, for example a lower alkanol, reducing inorganic salts, such as alkali metal iodides, for example sodium iodide, in the presence of a hydrogen donor, such as an acid, for example acetic acid, or a reducing sulphide compound, such as a di-lower alkyl sulphide, for example dimethyl sulphide, a reducing organic phosphorus compound, such as a phosphine, which optionally can contain substituted aliphatic or aromatic hydrocarbon radicals as substituents, such as trilower alkylphosphines, for example tri-n-butyl-phosphine, or triarylphosphines, for example triphenylphosphine, and also phosphites, which optionally contain substituted aliphatic hydrocarbon radicals as substituents, such as tri-lower alkylphosphites, usually in the form of corresponding alcohol adduct compounds, such as trimethyl-phosphite, or phosphorous acid triamides, which optionally contain substituted aliphatic hydrocarbon radicals as substituents, such as hexa-lower alkylphosphorous acid triamides, for example hexamethylphosphorous acid triamide, the latter preferably being in the form of a methanol adduct, or tetracyanoethylene. Splitting of the ozonide, which is usually not isolated, normally takes place under conditions which are employed for its manufacture, that is to say in the presence of a suitable solvent or solvent mixture and with cooling or slight warming.

Enol compounds of the formula VII can also be present in the tautomeric keto form.

An enol compound of the formula VIIa can be converted into a compound of the formula VIIb or VIc by reaction with a heavy metal sulphinate of the formula $M^{n+}(-SO_2-R_5)_n$ or, respectively, a heavy metal thiosulphonate of the formula $M^{n+}(-S-SO_2-R_5)_n$, analogously to the conversion of compounds of the formula Va to compounds of the formula Vb or Vc.

In a resulting compound of the formula VII, a group $R_1{}^a$, $R_1{}^b$ or $R_2{}^A$ can be converted into another group $R_1{}^a$, $R_1{}^b$ or $R_2{}^A$, for which analogous reactions can be used in those suitable for the conversion of these groups in the case of compounds of the formula IA or IB.

In the 4th stage, a resulting enol compound of the formula VII is converted into a compound of the formula VIII by esterification.

In order to manufacture sulphonic acid esters of the formula VIII, a compound of the formula VII is esterified with a reactive functional derivative of a sulphonic acid of the formula $HO-SO_2-R_5$, wherein $R_5$ has the meaning indicated for $R_5$ under Y.

Within the scope of meanings for $R_5$, these two groups can be either identical or different in a compound of the formula VIII.

The reactive functional derivatives of a sulphonic acid of the formula $HO-SO_2-R_5$ which are used are, for example, their reactive anhydrides, especially the mixed anhydrides with hydrogen halide acids, for example their chlorides, such as mesyl chloride and p-toluenesulphonic acid chloride.

The esterification is carried out, preferably in the presence of an organic tertiary nitrogen base, such as pyridine, triethylamine or ethyl-diisopropylamine, in a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofurane or dioxane, or in a solvent mixture, and, depending on the reactivity of the esterifying reagent, with cooling, at room temperature or with slight warming, that is to say at temperatures from about $-10°$ C. to about $+50°$ C., and also, if necessary, in a closed vessel and/or under an inert gas atmosphere, for example a nitrogen atmosphere.

The resulting sulphonic acid ester of the formula VIII can either be isolated or can be further processed in the same reaction mixture.

A compound of the formula VIIIa can be converted into a compound of the formula VIIIb or VIIIc by reaction with a heavy metal sulphinate of the formula $M^{n+}(-SO_2-R_5)_n$ or, respectively, a heavy metal thiosulphonate of the formula $M^{n+}(-S-SO_2-R_5)_n$, analogously to the conversion of compounds of the formula Va into compounds of the formula Vb and Vc respectively.

In a resulting compound of the formula VIII, a group $R_1{}^a$, $R_1{}^b$ or $R_2{}^A$ can be converted into another group $R_1{}^a$, $R_1{}^b$ or $R_2{}^A$, for which purpose it is possible to use analogous reactions to those indicated for the conversion of these groups in the case of compounds of the formula IA or V.

In the 5th stage, a resulting sulphonic acid ester of the formula VIII is converted into a compound of the formula II by treatment with a primary or secondary amine of the formula $H-N(R_4{}^a)(R_4{}^b)$.

The amination is carried out in a suitable inert organic solvent, such as an aliphatic, cycloaliphatic or aromatic hydrocarbon, such as hexane, cyclohexane, benzene or toluene, a halogenated aliphatic hydrocarbon, such as methylene chloride, or an ether, such as a di-lower alkyl ether, for example diethyl ether, or a cyclic ether, for example tetrahydrofurane or dioxane, or in a solvent mixture and, depending on the reactivity of the group $-O-SO_2-R_5$ and of the amine used, at temperatures between about $-10°$ C. and about 50° C., preferably at about 0° C. to about 20° C., if necessary in a closed vessel and/or under an inert gas atmosphere, for example a nitrogen atmosphere.

A compound of the formula II can also be obtained in stage 5a by treating a compound of the formula VII with a salt of a primary or secondary amine of the formula $H-N(R_4{}^a)(R_4{}^b)$, for example a hydrogen halide addition salt, such as a hydrochloride, in the presence of a tertiary base, such as pyridine, in a suitable solvent, such as a lower alcohol, for example absolute ethanol, at temperatures from about 20° to about 100° C., preferably from about 40° to about 60° C.

A compound of the formula IIa can be converted into a compound of the formula IIb or IIc by reaction with a heavy metal sulphinate of the formula $M^{n+}(-SO_2-R_5)_n$ or, respectively, a heavy metal thiosulphonate of the formula $M^{n+}(-S-SO_2-R_5)_n$, analogously to the conversion of compounds of the formula Va to compounds of the formula Vb and Vc respectively.

In a resulting compound of the formula II, it is possible, taking the enamine function into account, to convert a group $R_1{}^a$, $R_1{}^b$ or $R_2{}^A$ into another group $R_1{}^a$, $R_1{}^b$ or $R_2{}^A$.

The pharmacologically usable compounds of the present invention can, for example, be used for the manufacture of pharmaceutical preparations which contain an effective amount of the active substance together with, or mixed with, inorganic or organic, solid or liquid, pharmaceutically usable excipients which are suitable for enteral administration or preferably for parenteral administration. Thus, tablets or gelatine capsules are used which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as corn starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of injectable preparations, for example preparations which can be administered intravenously, or of infusion solutions. Such solutions are, preferably, isotonic aqueous solutions or suspensions and these can, for example, be manufactured before use from lyophilised preparations which contain the active substance by itself or together with an excipient, for example mannitol. The pharmaceutical preparations can be sterilised and/or contain auxiliaries, for example preservatives, stabilisers, wetting agents and/or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragée-making, dissolving or lyophilising processes, and contain from about 0.1% to 100%, especially from about 1% to about 50%, of lyophilised products or up to 100% of the active substance.

In the context of the present description, the organic radicals described as "lower" contain, unless expressly defined, up to 7, preferably up to 4, carbon atoms; acyl radicals contain up to 20, preferably up to 12 and above all up to 7, carbon atoms.

The examples which follow serve to illustrate the invention; temperatures are given in degreees Centigrade. The cephem compounds mentioned in the examples possess the R-configuration in the 6-position and 7-position and the azetidinone compounds mentioned in the examples possess the R-configuration in the 3-position and 4-position.

EXAMPLE 1

A solution of 160 mg (0.23 mmol) of a mixture consisting of 2-[4-(p-toluenesulphonylthio)-3-phenoxyacetamido-2-oxoazetidin-1-yl]-3-(1-pyrrolidyl)-crotonic acid p-nitrobenzyl ester and the corresponding isocrotonic acid ester in 3 ml of dry acetonitrile is heated under nitrogen for about 4 hours at 80° C. until no further starting material can be detected by thin layer chromatography (silica gel; toluene/ethyl acetate, 1:1). The heating bath is removed, p-toluenesulphonic acid (about 0.23 mmol) and 0.2 ml of water are added to the reaction mixture containing the 7β-phenoxyacetamido-3-pyrrolidino-cephem-4-carboxylic acid p-nitrobenzyl ester and the mixture is stirred for a further 2 hours at room temperature. The reaction mixture is diluted with benzene, washed with water, dried over sodium sulphate and evaporated in vacuo. The residue is triturated at 0° C. with diethyl ether and gives the pale yellow 7β-phenoxyacetamido-3-hydroxy-3-cephem-4-carboxylic acid p-nitrobenzyl ester.

IR spectrum (methylene chloride): characteristic bands at 2.95; 3.3; 5.6; 5.75 (sh); 5.9; 5.95 (sh); 6.55; 7.45; 8.15 and 8.3μ; NMR spectrum (deuterochloroform): δ in ppm: 3.4 (2H, 2, J=17 Hz); 4.57 (2H, s); 5.06 (1H, d; J=5 Hz); 5.35 (2H, q, J=14 Hz); 5.7 (1H, dd, J=5.10 Hz); 6.8–8.4 (10H, c) and 11.4 (1H, br.s.).

The starting materials can be obtained as follows:

(a) A solution of 36.6 g (0.1 mol) of 6-phenoxyacetamidopenicillanic acid 1β-oxide, 11.1 ml (0.11 mol) of triethylamine and 23.8 g (0.11 mol) of p-nitrobenzyl bromide in 200 ml of dimethylformamide is stirred under nitrogen for 4 hours at room temperature. The reaction solution is then introduced into 1.5 l of ice water and the precipitate is filtered off, dried and recrystallised twice from ethyl acetate/methylene chloride. The colourless crystalline 6-phenoxyacetamidopenicillanic acid p-nitrobenzyl ester 1β-oxide melts at 179°–180° C.

(b) A solution of 5.01 g (10 mmols) of 6-phenoxyacetamidopenicillanic acid p-nitrobenzyl ester 1β-oxide and 1.67 g (10 mmols) of 2-mercaptobenzthiazole in 110 ml of dry toluene is boiled under reflux in a nitrogen atmosphere for 4 hours. The solution is concentrated to about 25 ml by distillation and diluted with about 100 ml of ether. The product which has separated out is recrystallised from methylene chloride/ether and 2-[4-(benzthiazol-2-yldithio)-3-phenoxyacetamido-2-oxoazetidin-1-yl]-3-methylene-butyric acid p-nitrobenzyl ester of melting point 138°–141° C. is obtained.

(c) 1.06 g of finely powdered silver nitrate are added to a solution of 3.25 g (5.0 mmols) of 2-[4-(benzthiazol-2-yl-dithio)-3-phenoxyacetamido-2-oxoazetidin-1-yl]-3-methylenebutyric acid p-nitrobenzyl ester in 200 ml of acetone/water, 9:1 (v/v). Immediately afterwards, a solution of 890 mg (5 mmols) of sodium p-toluenesulphinate in 100 ml of the same solvent mixture is introduced (in the course of ten minutes). A pale yellow precipitate forms immediately. After stirring for one hour at room temperature, the mixture is filtered, with addition of Celite. The filtrate is diluted with water and extracted twice with ether. The combined ether extracts are dried over sodium sulphate and, after concentrating, give pale yellow, solid 2-[4-(p-toluenesulphonylthio)-3-phenoxyacetamido-2-oxoazetidin-1-yl]-3-methylenebutyric acid p-nitrobenzyl ester. Thin layer chromatogram on silica gel (toluene/ethyl acetate, 2:1): Rf value 0.24; IR spectrum (in CH₂Cl₂): characteristic bands at 3.90, 5.56, 5.70, 5.87, 6.23, 6.53, 6.66, 7.40, 7.50, 8.10, 8.72, 9.25 and 10.95μ. The product can be employed without further purification in the subsequent reaction.

The same compound can also be obtained in accordance with the following methods:

(ci) 1.58 g (1.2 equivalents) of silver p-toluenesulphinate are added in portions, in the course of 10 minutes, to a solution of 3.25 g (5.0 mmols) of 2-[4-(benzthiazol-2-yldithio)-3-phenoxyacetamido-2-oxoazetidin-1-yl]-3-methylenebutyric acid p-nitrobenzyl ester in 200 ml of acetone/water, 8:1 (v/v). The suspension is stirred for one hour at room temperature, filtered and further processed as described in Example 1c). 2-[4-(p]Toluenesulphonylthio)-3-phenoxyacetamido-2-oxoazetidin-1-yl]-3-methylenebutyric acid p-nitrobenzyl ester is obtained in quantitative yield.

Silver p-toluenesulphinate is obtained as a colourless precipitate by combining aqueous solutions of equimolar amounts of silver nitrate and sodium p-toluenesulphinate. The product is dried in vacuo for 24 hours.

(cii) 2-[4-(p-Toluenesulphonylthio)-3-phenoxyacetamido-2-oxoazetidin-1-yl]-3-methylenebutyric acid p-nitrobenzyl ester can also be obtained, in quantitative yield, analogously to Example 1(ci) from 3.25 g of 2-[4-(benzthiazol-2-yldithio)-3-phenoxyacetamido-2-oxoazetidin-1-yl]-3-methylenebutyric acid p-nitrobenzyl ester and 1.87 g (2 equivalents) of copper-II di-p-toluenesulphinate.

Copper-II di-p-toluenesulphinate is obtained by reacting copper sulphate and sodium p-toluenesulphinate (2 equivalents) in water. After filtering off, the salt is dried in vacuo for 12 hours at 60° C.

(ciii) 2-[4-(p-Toluenesulphonylthio)-3-phenoxyacetamido-2-oxoazetidin-1-yl]-3-methylenebutyric acid p-nitrobenzyl ester can also be obtained analogously to Example 1(ci) from 130 mg of 2-[4-(benzthiazol-2-yldithio)-3-phenoxyacetamido-2-oxoazetidin-1-yl]-3-methylenebutyric acid p-nitrobenzyl ester and 85 mg (2 equivalents) of tin-II di-p-toluenesulphinate.

Tin-II di-p-toluenesulphinate is obtained by reacting tin-II chloride (2H₂O) and sodium p-toluenesulphinate in water. After filtering off and washing with water, the salt is dried in vacuo for about 12 hours at 50°–60° C.

(civ) 2-[4-(p-Toluenesulphonylthio)-3-phenoxyacetamido-2-oxoazetidin-1-yl]-3-methylenebutyric acid p-nitrobenzyl ester can also be obtained analogously to Example 1(ci) from 130 mg of 2-[4-(benzthiazol-2-yldithio)-3-phenoxyacetamido-2-oxoazetidin-1-yl]-3-methylenebutyric acid p-nitrobenzyl ester and 102 mg (2 equivalents) of mercury-II di-p-toluenesulphinate.

Mercury-II di-p-toluenesulphinate is obtained by reacting mercury-II diacetate and sodium p-toluenesulphinate in water. After filtering off and washing with water, the salt is dried in vacuo for about 12 hours at 50°-60° C.

(cv) A solution of 517 mg (1.02 mmols) of 6-phenoxyacetamidopenicillanic acid p-nitrobenzyl ester 1β-oxide and 187 mg (1.2 mmols) of p-toluenesulphinic acid in 10 ml of 1,2-dimethoxyethane (or dioxane) is heated under reflux for 4.5 hours in the presence of 3.5 g of a 3A molecular sieve and in a nitrogen atmosphere, after which a further 308 mg (1.98 mmols) of p-toluenesulphinic acid, dissolved in 2 ml of 1,2-dimethoxyethane, are added in five portions at 45 minute intervals. After 4.5 hours the reaction mixture is poured into 100 ml of 5% strength aqueous sodium bicarbonate solution and the mixture is extracted with ethyl acetate. The combined organic phases are washed with water and saturated aqueous sodium chloride solution, dried over magnesium sulphate and evaporated. The residue is chromatographed on silica gel thick layer plates with toluene/ethyl acetate, 2:1, and gives 2-[4-(p-toluenesulphonylthio)-3-phenoxyacetamido-2-oxoazetidin-1-yl]-3-methylenebutyric acid p-nitrobenzyl ester.

(cvi) A mixture of 250 mg (0.5 mmol) of 6-phenoxyacetamidopenicillanic acid p-nitrobenzyl ester 1β-oxide, 110 mg (0.61 mmol) of p-toluenesulphonyl cyanide and 5 mg (0.022 mmol) of benzyl-triethylammonium chloride in 2 ml of dry, peroxide-free dioxane is stirred under argon for 4.5 hours at 110° C. The solvent is evaporated off in vacuo and the residual yellow oil is chromatographed on acid-washed silica gel. Elution with 30% ethyl acetate in toluene gives 2-[4-(p-toluenesulphonylthio)-3-phenoxyacetamido-2-oxoazetidin-1-yl]-3-methylenebutyric acid p-nitrobenzyl ester.

(cvii) A mixture of 110 mg (0.61 mmol) of p-toluenesulphonyl cyanide and 4.5 mg (0.021 mmol) of tetraethylammonium bromide in 1 ml of pure dioxane is stirred at 110° C. for 30 minutes, under argon. A suspension of 250 mg (0.5 mmol) of 6-phenoxyacetamidopenicillanic acid p-nitrobenzyl ester 1β-oxide in 1 ml of dioxane is then added and the resulting solution is stirred for 4 hours at 110° C., under argon. The solvent is removed in vacuo, the crude product is dissolved in ethyl acetate and the solution is washed with water and saturated aqueous sodium chloride solution. The organic phase is dried with magnesium sulphate and freed from solvent in vacuo and gives crude 2-[4-(p-toluenesulphonylthio)-3-phenoxyacetamido-2-oxoazetidin-1-yl]-3-methylenebutyric acid p-nitrobenzyl ester.

(d) 1.1 equivalents of ozone are passed into a solution of 1.92 g (3.0 mmols) of 2-[4-(p-toluenesulphonylthio)-3-phenoxyacetamido-2-oxoazetidin-1-yl]-3-methylenebutyric acid p-nitrobenzyl ester in 30 ml of dry methyl acetate, at −78° C., in the course of 33 minutes. Immediately thereafter, excess ozone is removed by means of a stream of nitrogen (15 minutes at −78° C.). 2.2 ml of dimethyl sulphide (10 equivalents) are added and the solution is warmed to room temperature. After leaving to stand for 5 hours, the solvent is distilled off in vacuo and the residual colourless oil is taken up in 100 ml of benzene. The benzene solution is washed with three 50 ml portions of saturated sodium chloride solution, dried over magnesium sulphate and concentrated to dryness in vacuo. After recrystallising the residue from toluene, 2-[4-(p-toluenesulphonylthio)-3-phenoxyacetamido-2-oxoazetidin-1-yl]-3-hydroxycrotonic acid p-nitrobenzyl ester of melting point 159°-160° C. is obtained.

(di) The crude 2-[4-(p-toluenesulphonylthio)-3-phenoxyacetamido-2-oxoazetidin-1-yl]-3-methylenebutyric acid p-nitrobenzyl ester, obtained according to Example 1.(cvii), is dissolved in 20 ml of methyl acetate and ozonised at −70° C. until no further starting material is present, according to a thin layer chromatogram. A stream of nitrogen is then passed through the solution and the latter is warmed to 0°-5° C. A solution of 300 mg of sodium bisulphite in 5 ml of water is added and the mixture is stirred for about 5 minutes until no further ozonide can be detected with potassium iodide/starch paper. The mixture is diluted with ethyl acetate, the aqueous phase is separated off, and the organic phase is washed with water, dried over magnesium sulphate and freed from solvent in vacuo. The crude product is dissolved in 3 ml of methylene chloride and 15 ml of toluene are added. The precipitate is filtered off and the filtrate is evaporated in vacuo. The residue is recrystallised from methanol and gives 2-[4-(p-toluenesulphonylthio)-3-phenoxyacetamido-2-oxoazetidin-1-yl]-3-hydroxycrotonic acid p-nitrobenzyl ester of melting point 159°-160° C.

(e) A solution of 641 mg (1 mmol) of 2-[4-(p-toluenesulphonylthio)-3-phenoxyacetamido-2-oxoazetidin-1-yl]-3-hydroxycrotonic acid p-nitrobenzyl ester in 5 ml of dry pyridine is cooled to −10° C. in an acetone/ice bath, 285 mg (1.5 mmols) of p-toluenesulphonyl chloride are added and the mixture is stirred under a nitrogen atmosphere for about 5 hours until no further starting material can be detected by thin layer chromatography (silica gel: toluene/ethyl acetate, 1:1). The reaction solution is diluted with 50 ml of benzene, washed with water, ice-cold 10% strength aqueous citric acid solution and saturated aqueous sodium chloride solution, dried over sodium sulphate and evaporated in vacuo. This gives pale yellow coloured 2-[4-(p-toluenesulphonylthio)-3-phenoxyacetamido-2-oxoazetidin-1-yl]-3-p-toluenesulphonyloxy-crotonic acid p-nitrobenzyl ester, which is sufficiently pure for further processing. IR spectrum (methylene chloride): characteristic bands at 5.6; 5.8; 5.9; 6.55; 7.45; 8.55 and 8.75μ; NMR spectrum (deuterochloroform): δ in ppm: 2.4 (6H, s); 2.45 (3H, s); 4.4 (2H, q, J=15 Hz); 5.3 (2H, s); 5.3 (1H, dd, J=5.10 Hz); 5.8 (1H d; J=5 Hz) and 6.6-8.4 (18H, c)f) A solution of 80 mg (0.1 mmol) of 2-[4-(p-toluenesulphonylthio)-3-phenoxyacetamido-2-oxoazetidin-1-yl]-3-p-toluenesulphonyloxy-crotonic acid p-nitrobenzyl ester and 0.0175 ml of pyrrolidine (0.21 mmol) in 2 ml of dry tetrahydrofurane is stirred for about 1 hour under a nitrogen atmosphere until no further starting material can be detected by thin layer chromatography (silica gel: toluene/ethyl acetate, 1:1). The reaction mixture is diluted with 10 ml of benzene, washed with twice 5 ml of saturated aqueous sodium chloride solution, dried over sodium sulphate and evaporated in vacuo. The residue is chromatographed on silica gel thick layer plates with toluene/ethyl acetate, 1:1, and gives a mixture consisting of colourless 2-[4-(p-toluenesulphonylthio)-3-phenoxyacetamido-2-oxoazetidin-1-yl]-3-(1-pyrrolidyl)crotonic acid p-nitrobenzyl ester and the corresponding isocrotonic acid ester. IR spectrum (methylene chloride): characteristic bands at 5.6; 5.95; 6.55; 7.45 and 8.75μ; NMR spectrum (deuterochloroform): δ in ppm: 1.6-2.2 and 3.0-3.8 (8H, c); 2.08 and 2.27 (3H, s); 2.38 and 2.39 (3H, s); 4.42 (2H, q, J=15 Hz); 4.8–6.0 (4H, c) and 6.6–8.4 (14H, c).

The same compounds can also be obtained as follows:

(fi) A solution, cooled to −10° C., of 256 mg (0.4 mmol) of 2-[4-(p-toluenesulphonylthio)-3-phenoxyacetamido-2-oxoazetidin-1-yl]-3-hydroxycrotonic acid p-nitrobenzyl ester in 5 ml of dry methylene chloride is treated, under nitrogen, with 0.1115 ml (0.8 mmol) of triethylamine and then with 0.062 ml (0.8 mmol) of methanesulphonyl chloride. After one hour, 0.104 ml (1.24 mmols) of freshly distilled pyrrolidine is added and the mixture is stirred for a further 2 hours at −10° C. The reaction solution is diluted with 20 ml of methylene chloride, washed with three times 15 ml of water, dried over sodium sulphate and evaporated in vacuo. The residue is triturated with diethyl ether and gives a mixture which consists of pale yellow 2-[4-(p-toluenesulphonylthio)-3-phenoxyacetamido-2-oxoazetidin-1-yl]-3-(1-pyrrolidyl)crotonic acid p-nitrobenzyl ester and the corresponding isocrotonic acid p-nitrobenzyl ester and which can be employed in this form in the next stage.

The methanesulphonic acid ester which is formed as an intermediate product can also be isolated or prepared as follows:

(fii) A solution, cooled to −10° C., of 128 mg (0.2 mmol) of 2-[4-(p-toluenesulphonylthio)-3-phenoxyacetamido-2-oxoazetidin-1-yl]-3-hydroxycrotonic acid p-nitrobenzyl ester in 1 ml of dry methylene chloride is treated, under nitrogen, with 0.042 ml (0.3 mmol) of triethylamine and 0.017 ml (0.22 mmol) of methanesulphonyl chloride and the mixture is stirred for 30 minutes at the same temperature. The reaction mixture is diluted with 10 ml of methylene chloride, washed with 3 times 10 ml of saturated aqueous sodium chloride solution, dried over sodium sulphate and evaporated in vacuo. The residue, which contains 2-[4-(p-toluenesulphonylthio)-3-phenoxyacetamido-2-oxoazetidin-1-yl]-3-methanesulphonyloxy-crotonic acid p-nitrobenzyl ester and the corresponding isocrotonic acid ester, cannot easily be purified by chromatography because of instability but is sufficiently pure to enable it to be further processed [for example according to Example 1(fi)].

IR spectrum (methylene chloride): characteristic bands at 5.55; 5.7; 5.8; 6.55; 7.45; 8.55 and 8.75µ; NMR spectrum (deuterochloroform): δ in ppm: 2.37 (3H, s); 2.39 and 2.5 (3H, s); 3.12 and 3.27 (3H, s); 4.39 and 4.41 (2H, s); 5.2 (1H dd, J=5.10 Hz); 5.25 (2H, s); 5.88 and 5.95 (1H, d, J=5 Hz) and 6.6–8.4 (15H, c).

EXAMPLE 2

A solution of 148 mg (0.2 mmol) of a mixture consisting of 2-[4-(p-toluenesulphonylthio)-3-phenoxyacetamido-2-oxoazetidin-1-yl]-3-(N-methylcyclohexylamino)-crotonic acid p-nitrobenzyl ester and the corresponding isocrotonic acid ester, in 3 ml of dry acetonitrile, is heated under nitrogen for about 4 hours at 80° C. until no further starting material can be detected by thin layer chromatography (silica gel: toluene/ethyl acetate, 1:1). The heating bath is removed, 38 mg (0.2 mmol) of p-toluenesulphonic acid and about 0.2 ml of water are added to the reaction mixture and the mixture is stirred for a further 2 hours at room temperature. The reaction mixture is diluted with benzene, washed with water, dried over sodium sulphate and evaporated in vacuo. The residue is triturated at 0° C. with diethyl ether and gives pale yellow 7β-phenoxyacetamido-3-hydroxy-3-cephem-4-carboxylic acid p-nitrobenzyl ester. IR spectrum (methylene chloride): characteristic bands at 2.95; 3.3; 5.6; 5.75 (sh); 5.9; 5.95 (sh); 6.55, 7.45, 8.15 and 8.3µ; NMR spectrum (deuterochloroform): δ in ppm: 3.4 (zH, q, J=17 Hz); 4.57 (2H, s); 5.06 (1H, d; J=5 Hz); 5.35 (2H, q, J=14 Hz) 5.7 (1H dd, J=5, 10 Hz); 6.8–8.4 (10H, c) and 11.4 (1H, br.s.).

The starting material can be obtained as follows:

0.056 ml (0.42 mmol) of N-methyl-N-cyclohexylamine are added to a solution of 160 mg (0.2 mmol) of 2-[4-(p-toluenesulphonylthio)-3-phenoxyacetamido-2-oxoazetidin-1-yl]-3-p-toluenesulphonyloxy-crotonic acid p-nitrobenzyl ester in 2 ml of dry tetrahydrofurane, in a nitrogen atmosphere and whilst stirring, and the mixture is stirred for about a further 2 hours at room temperature until no further starting material can be detected by thin layer chromatography (silica gel: toluene/ethyl acetate, 1:1). The reaction solution is diluted with benzene, washed several times with water, dried over sodium sulphate and evaporated in vacuo. The residue is chromatographed on 10 g of acid-washed silica gel with benzene/ethyl acetate, 3:1. A mixture consisting of 2-[4-(p-toluenesulphonylthio)-3-phenoxyacetamido-2-oxoazetidin-1-yl]-3-(N-methylcyclohexyylamino)-crotonic acid p-nitrobenzyl ester and the corresponding isocrotonic acid ester is obtained as a pale yellow oil. IR spectrum (methylene chloride): characteristic bands at 2.95; 3.4; 5.6; 5.8; 6.55; 7.4 and 8.75µ.

EXAMPLE 3

Analogously to Example 1, it is possible, starting from a mixture consisting of 2-[4-p-(toluenesulphonylthio)-3-phenoxyacetamido)-2-oxoazetidin-1-yl]-3-cyclohexylaminocrotonic acid p-nitrobenzyl ester and the corresponding isocrotonic acid ester, to prepare 7β-phenoxyacetamido-3-cyclohexylamino-cephem-4-carboxylic acid p-nitrobenzyl ester (a mixture of 2- and 3-cephem derivatives) and from this to prepare 7β-phenoxyacetamido-3-hydroxy-3-cephem-4-carboxylic acid p-nitrobenzyl ester.

The starting material can be obtained as follows:

(a) A solution of 160 mg (0.2 mmol) of 2-[4-p-(toluenesulphonylthio)-3-phenoxyacetamido)-2-oxoazetidin-1-yl]-3-p-toluenesulphonyloxy-crotonic acid p-nitrobenzyl ester in 2 ml of dry tetrahydrofurane is treated, under nitrogen, with 0.0577 ml (0.5 mmol) of cyclohexylamine and the mixture is stirred for 1 hour at room temperature. The reaction solution is diluted with benzene, washed with water, dried over sodium sulphate and evaporated in vacuo. The residue, which contains a mixture consisting of 2-[4-p-(toluenesulphonylthio)-3-phenoxyacetamido)-2-oxoazetidin-1-yl]-3-cyclohexylamino-crotonic acid p-nitrobenzyl ester and the corresponding isocrotonic acid ester, can be further processed without purification. IR spectrum (methylene chloride): characteristic bands at 2.9; 3.4; 5.6; 5.9; 6.0; 6.25; 6.55; 7.45; 8.10 and 8.75µ; NMR spectrum (deuterochloroform): δ in ppm: 1.8–2.0 (11H, c) 2.02 (3H, s); 2.35 (3H, s); 4.43 (2H, s); 4.95 (1H dd, J=5.10 Hz); 5.17 (2H, s); 5.80 (1H, d, J=5 Hz) and 6.6–9.2 (15H, c).

EXAMPLE 4

(a) 3 ml of an ethereal diazomethane solution (0.5 molar, 1.5 equivalents) are added in the course of about 10 minutes to a solution, cooled to 0° C., of 485 mg of 7β-phenoxyacetamido-3-hydroxy-3-cephem-4-carboxylic acid p-nitrobenzyl ester in 10 ml of dry chloroform.

The pale yellow solution is stirred for 1 hour at 0° C., flushed with nitrogen in order to remove excess diazomethane and concentrated in vacuo. The residue is recrystallised from methylene chloride and gives 7β-phenoxyacetamido-3-methoxy-3-cephem-4-carboxylic acid p-nitrobenzyl ester of melting point 140.5°–142° C.

The same compound can also be obtained by means of phase transfer catalysis, as follows:

(ai) A suspension of 4.85 g of 7β-phenoxyacetamido-3-hydroxy-3-cephem-4-carboxylic acid p-nitrobenzyl ester in 25 ml of carbon tetrachloride and 27 ml of water is treated, at 20°, whilst stirring vigorously, successively with 3.0 g of potassium bicarbonate, 3.8 ml of dimethyl sulphate and 1.93 g of tetrabutylammonium bromide. The mixture is stirred vigorously for 4 hours at 20°. After diluting with 50 ml of water, the mixture is extracted with twice 50 ml of methylene chloride. 7β-Phenoxyacetamido-3-methoxy-3-cephem-4-carboxylic acid p-nitrobenzyl ester is obtained by evaporating the extracts, previously dried over sulphate, and crystallising the residue from methylene chloride/diethyl ether.

(b) A solution of 250 mg (0.5 mmol) of 7β-phenoxyacetamido-3-methoxy-3-cephem-4-carboxylic acid p-nitrobenzyl ester in 2 ml of methanol/tetrahydrofuran, 1:1, is added to a mixture of 5% palladium/charcoal in 2 ml of the same solvent, which mixture has been prehydrogenated for one hour under atmospheric pressure, and the reaction mixture is hydrogenated for 3 hours at room temperature and under atmospheric pressure. After this time, about 90% of the calculated amount of hydrogen has been taken up. The catalyst is filtered off and the filtrate is evaporated in vacuo. The residue is taken up in 10 ml of methylene chloride and extracted with twice 10 ml of 5% strength aqueous sodium bicarbonate solution. The combined bicarbonate extracts are neutralised at 0° C. with dilute hydrochloric acid and extracted with 3 times 10 ml of methylene chloride. The organic phase is dried over sodium sulphate and freed from the solvent in vacuo. After crystallisation from chloroform/pentane, the residue gives 7β-phenoxyacetamido-3-methoxy-3-cephem-4-carboxylic acid of melting point 173°–174° C.

(c) 0.7 ml (5.7 mmols) of dimethyl-dichlorosilane are added to a suspension of 2.55 g (7 mmols) of 7β-phenoxyacetamido-3-methoxy-ceph-3-em-4-carboxylic acid and 2.9 ml (22.4 mmols) of N,N-dimethylaniline in 11 ml of absolute methylene chloride, under nitrogen at 20° C., and the mixture is then stirred for 30 minutes at the same temperature. The resulting clear solution is cooled to −20° C., 1.6 g (7.7 mmols) of solid phosphorus pentachloride are added and the mixture is stirred for 30 minutes. A pre-cooled (−20° C.) mixture of 0.9 ml (7 mmols) of N,N-dimethylaniline and 0.9 ml of n-butanol is added at the same temperature in the course of 2 to 3 minutes, 10 ml of pre-cooled (−20° C.) of n-butanol are then added rapidly and the mixture is then stirred for 20 minutes at −20° C. and for 10 minutes without cooling. 0.4 ml of water is added at about −10° C., the mixture is stirred for about 10 minutes in an ice bath (0° C.), 11 ml of dioxane are then added and, after stirring for a further 10 minutes at 0° C., about 4.5 ml of tri-n-butylamine are added in portions until samples diluted with water assume a constant pH value of 3.5. After stirring for 1 hour at 0° C., the precipitate is filtered off, washed with dioxane and recrystallised from water/dioxane. The resulting 7β-amino-3-methoxh-ceph-3-em-4-carboxylic acid hydrochloride dioxanate has a melting point of above 300° C. Thin layer chromatogram: Rf value 0.17 (silica gel; system, n-butanol/carbon tetrachloride/methanol/formic acid/water, 30:40:20:5:5).

(ci) A suspension of 11.75 g of 93 percent strength (corresponding to 10.93 g of 100% strength) of 7β-phenoxyacetamido-3-methoxy-ceph-3-em-4-carboxylic acid and 13.4 ml (12.73 g) of N,N-dimethylaniline in 47 ml of absolute methylene chloride (distilled over $P_2O_5$) is treated, at +20° C., under nitrogen, with 3.6 ml (3.87 g) of dimethyldichlorosilane and the mixture is then stirred for 30 minutes at the same temperature. The solution, which is now clear, is cooled to −18°/−19° and 7.8 g of solid phosphorus pentachloride are added, the internal temperature rising to −10°. After stirring for 30 minutes in a bath at −20°, the clear solution is added dropwise, in the course of about 7 minutes, to a mixture, cooled to −20°, of 47 ml of n-butanol (anhydrous, dried over Sikkan) and 4.4 ml (4.18 g) of dimethylaniline. The internal temperature rises to −8°. The mixture is stirred for a further 30 minutes, initially in a bath at −20° and subsequently in an ice bath (0°), so that a final internal temperature of −10° is reached. A mixture of 47 ml of dioxane and 1.6 ml of water is added dropwise at this temperature (time taken, about 5 minutes). The product thereupon crystallises out slowly. After stirring for a further 10 minutes, the pH of the mixture, in an ice bath, is brought to a value of between 2.2 and 2.4, and kept at this value, by adding about 9.5 ml of tri-n-butylamine, in portions, in the course of about 1 hour (the first 3 ml are added in the first 5 minutes). The product is then filtered off, washed, in portions, with about 30 ml of dioxane and then with about 15 ml of methylene chloride and crystalline 7β-amino-3-methoxy-ceph-3-em-4-carboxylic acid hydrochloride dioxanate is thus obtained; melting point above 300° C.; UV spectrum (in 0.1N sodium bicarbonate): $\lambda_{max}=270$ mμ ($\epsilon=7,600$); IR spectrum (nujol): characteristic bands at 5.62; 5.80; 5.88; 6.26; 6.55; 7.03; 7.45; 7.72; 7.96; 8.14; 8.26; 8.45; 8.64; 8.97; 9.29; 10.40 and 11.47 mμ; $[\alpha]_D^{20}=+134°\pm1°$ (c=1; 0.5N sodium bicarbonate solution).

The zwitter ion of 7β-amino-3-methoxy-ceph-3-em-4-carboxylic acid can be obtained from the resulting hydrochloride dioxanate by treating a 20% strength aqueous solution of the latter with 2N sodium hydroxide solution until the pH reaches a value of 4.1 (isoelectric point); when filtered off and dried, the zwitter ion has a melting point of above 300° C. UV spectrum (in 0.1N sodium bicarbonate solution) $\lambda_{max}=270$ nm ($\epsilon=7,600$). Thin layer chromatogram: Rf value identical to that of the hydrochloride (silica gel, same system); $[\alpha]_D^{20}=+232°\pm1°$ (c=1; 0.5N sodium bicarbonate solution).

(d) 1.65 ml of bis-(trimethylsilyl)-acetamide are added to a suspension of 1 g of (2.82 mmols) of 7β-amino-3-methoxy-ceph-3-em-4-carboxylic acid hydrochloride dioxanate in 20 ml of dry methylene chloride, at room temperature under a nitrogen atmosphere. After 40 minutes, the clear solution is cooled to 0° C. and 900 mg (4.37 mmols) of solid D-α-phenylglycyl acid chloride hydrochloride are added. Five minutes later, 0.7 ml (10 mmols) of propylene oxide are added. The suspension is then stirred for 1 hour at 0° C. under a nitrogen atmosphere, after which 0.5 ml of methanol are added, whereupon 7β-(D-α-phenylglycylamino)-3-methoxy-ceph-3-em-4-carboxylic acid hydrochloride precipitates in a crystalline form. The hydrochloride is filtered off and dissolved in 9 ml of water and the pH of the solution is adjusted to 4.6 with 1N sodium hydroxide solution. The dihydrate of the inner salt of 7β-(D-α-phenylglycylamino)-3-methoxy-ceph-3-em-4-carboxylic acid, which precipitates out, is filtered off, washed with acetone and diethyl ether and dried; melting point 174°–176° (decomposition); $[\alpha]_D^{20} = +132°$ (c=0.714; in 0.1N hydrochloric acid); thin layer chromatogram (silica gel): Rf value ~0.18 (system: n-butanol/acetic acid/water, 67:10:23). UV spectrum (in 0.1N aqueous sodium bicarbonate solution) $\lambda_{max} = 269\mu$ ($\epsilon = 7,000$); IR spectrum (in mineral oil): characteristic bands at 5.72, 5.94, 6.23 and 6.60μ.

(di) 1.37 ml (5.6 mmols) of N,N-bis-(trimethylsilyl)acetamide are added to a suspension of 993 mg (4.32 mmols) of 7β-amino-3-methoxy-ceph-3-em-4-carboxylic acid (inner salt) in 10 ml of methylene chloride and the mixture is stirred for 45 minutes at room temperature under a nitrogen atmosphere. The clear solution is cooled to 0° C. and 1.11 g (5.4 mmols) of D-α-phenylglycyl acid chloride hydrochloride are added. After 5 minutes, 0.4 ml (5.6 mmols) of propylene oxide is added. The suspension is then stirred for 1 hour at 0° C. under a nitrogen atmosphere and subsequently 0.6 ml of methanol is added. 7β-(D-α-Phenylglycylamido)-3-methoxy-ceph-3-em-4-carboxylic acid hydrochloride which crystallises out, is filtered off and dissolved in 15 ml of water at 0° C. and the pH of the solution is adjusted to about 4 with 5 ml of 1N sodium hydroxide solution. The pH of the solution, which is warmed to room temperature, is brought to about 4.8 with triethylamine, whereupon 7β-(D-α-phenylglycylamido)-3-methoxy-ceph-3-em-4-carboxylic acid crystallises out in the form of the dihydrate.

EXAMPLE 5

A solution of 158.2 g (0.2 mol) of a mixture consisting of 2-[4-(p-toluenesulphonylthio)-3-phenoxyacetamido-3-oxoazetidin-1-yl]-3-(1-pyrrolidyl)-crotonic acid diphenylmethyl ester and the corresponding isocrotonic acid ester in 1,500 ml of dry acetonitrile is heated under nitrogen for about 5 hours at 80° C. until no further starting material can be detected by thin layer chromatography (silica gel; toluene/ethyl acetate, 1:1). The heating bath is removed and the reaction mixture, which contains 7β-phenoxyacetamido-3-pyrrolidinocephem-4-carboxylic acid diphenylmethyl estter, is treated with 200 ml of 0.1N HCl and stirred for a further 3 hours at room temperature. The reaction mixture is evaporated in vacuo.

The residue is taken up in ethyl acetate, washed successively with dilute sulphuric acid, water, saturated aqueous sodium bicarbonate and saturated aqueous sodium chloride solution and dried over sodium sulphate. The solution is evaporated in vacuo and the crude 7β-phenoxyacetamido-3-hydroxy-3-cephem-4-carboxylic acid diphenylmethyl ester is purified by means of column chromatography (silica gel; toluene/ethyl acetate, 4:1); thin layer chromatogram: Rf value 0.24 (silica gel; toluene/ethyl acetate, 1:1).

The resulting product can be further processed as follows:

(i) The resulting 7β-phenoxyacetamido-3-hydroxy-3-cephem-4-carboxylic acid diphenylmethyl ester is taken up in methanol and treated, at 0° C., with an excess of an ethereal solution of diazomethane. After a reaction time of 5 minutes, the solution is concentrated completely and the oily residue is chromatographed on silica gel thick layer plates (toluene/ethyl acetate, 3:1). The silica gel in the zone at Rf=0.19 is extracted with ethyl acetate and gives 7β-phenoxyacetamido-3-methoxy-ceph-3-em-4-carboxylic acid diphenylmethyl ester; melting point 120° C. (from ether), IR spectrum (in CHCl₃); 3310, 1775, 1700, 1690 and 1600 cm⁻¹.

(ii) It is also possible, analogously to Example 4(ai), to convert the resulting 7β-phenoxyacetamido-3-hydroxy-3-cephem-4-carboxylic acid diphenylmethyl ester into the 7β-phenoxyacetamido-3-methoxy-ceph-3-em-4-carboxylic acid diphenylmethyl ester by means of dimethyl sulphate and potassium bicarbonate according to the phase transfer method.

(iii) 0.87 ml of anisole is added to a solution of 2.0 g (3.78 mmols) of 7β-phenoxyacetamido-3-methoxy-ceph-3-em-4-carboxylic acid diphenylmethyl ester in 5 ml of methylene chloride and the mixture is cooled to 0° C. and, after adding 1.2 ml of trifluoroacetic acid, left to stand for 1 hour. The reaction mixture is concentrated in vacuo and the residue is crystallised from acetone/ether. 7β-Phenoxyacetamido-3-methoxy-ceph-3-em-4-carboxylic acid of melting point 170° C. (decomposition) is obtained.

The starting material can be prepared as follows:

(a) 6-Phenoxyacetamidopenicillanic acid diphenylmethyl ester 1β-oxide of melting point 144°–146° C. (ethyl acetate/petroleum ether), is obtained from 100 g (27.3 mmols) of 6-phenoxyacetamidopenicillanic acid 1β-oxide, 500 ml of dioxane and 58.4 g (30 mmols) of diphenylmethyldiazomethane after about 2 hours.

(b) Analogously to Example 1b), 2-[4-(benzthiazol-2-yl-dithio)-3-phenoxyacetamido-2-oxoazetidin-1-yl]-3-methylenebutyric acid diphenylmethyl ester, of melting point 140°–141° C. (from toluene/ether), is obtained from 292 g (55 mmols) of 6-phenoxyacetamidopenicillanic acid diphenylmethyl ester 1β-oxide and 99 g (59.5 mmols) of 2-mercaptobenzthiazole.

(c) Analogously to Example 1(c), 2-[4-(p-toluenesulphonylthio)-3-phenoxyacetamido-2-oxoazetidin-1-yl]-3-methylenebutyric acid diphenylmethyl ester is obtained from 10 g (14.7 mmols) of 2-[4-(benzthiazol-2-yldithio)-3-phenoxyacetamido-2-oxoazetidin-1-yl]-3-methylenebutyric acid diphenylmethyl ester in 50 ml of ethyl acetate and 4.92 g (24.98 mmols) of finely powdered silver p-toluenesulphinate after stirring for 7 hours at room temperature. Rf value=0.28 (silica gel, toluene/ether acetate, 3:1); IR spectrum (CHCl₃): 1782, 1740, 1695, 1340 and 1150 cm⁻¹.

(d) Analogously to Example 1d), 2-[4-(p-toluenesulphonylthio)-3-phenoxyacetamido-2-oxoazetidin-1-yl]-3-hydroxycrotonic acid diphenylmethyl ester of melting point 142°–143° C. (from ether/pentane), is obtained from 10.8 g (16.2 mmols) of 2-84-(p-toluenesulphonylthio)-3-phenoxyacetamido-2-oxoazetidin-1-yl]-3-methylenebutyric acid diphenylmethyl ester in 1 l of methylene chloride and 1.1 equivalents of ozone.

(e) A solution, cooled to −10° C., of 134.4 g (0.2 mol) of 2-[4-(p-toluenesulphonylthio)-3-phenoxyacetamido-2-oxoazetidin-1-yl]-3-hydroxycrotonic acid diphenylmethyl ester in 500 ml of dry methylene chloride is treated, under nitrogen, with 34.8 ml (0.25 mol) of triethylamine and then with 24.5 ml (0.25 mol) of methanesulphonyl chloride. After 20 minutes, 47 ml (0.55 mol) of freshly distilled pyrrolidine are added and the mixture is stirred for a further 2½ hours at −10° C. The reaction solution is washed with three times 150 ml of water, dried over sodium sulphate and evaporated in vacuo. The residue is dried to a foam and gives a mixture which consists of pale yellow 2-[4-(p-toluenesulphonylthio)-3-phenoxyacetamido-2-oxoazetidin-1-yl]-3-

(1-pyrrolidyl)-crotonic acid diphenylmethyl ester and the corresponding isocrotonic acid diphenylmethyl ester and which can be employed in this form in the next stage.

EXAMPLE 6

Analogously to Example 4d, it is possible, by reacting 1.16 g (3 mmols) of 7β-amino-3-methoxy-ceph-3-em-4-carboxylic acid hydrochloride dioxanate, which is obtainable according to the invention, with 1.5 ml (6.2 mmols) of bis-(trimethylsilyl)acetamide and subsequently reacting the reaction product (a) with 765 mg (3.6 mmols) of D-α-amino-(2-thienyl)-acetic acid chloride hydrochloride, to obtain 7β-[D-α-amino-α-(2-thienyl)-acetylamino]-3-methoxy-3-cephem-4-carboxylic acid in the form of the inner salt, melting point 140° (with decomposition); thin layer chromatogram (silica gel; identification with iodine): Rf~0.22 (system: n-butanol/acetic acid/water, 67:10:23) and Rf~0.53 (systems: isopropanol/formic acid/water, 77:4:19); ultraviolet absorption spectrum: $\lambda_{max}=235$ mµ ($\epsilon=11,400$) and $\lambda_{shoulder}=272$ mµ ($\delta=6,100$) in 0.1N hydrochloric acid, and $\lambda_{max}=238$ mµ ($\epsilon=11,800$) and $\lambda_{shoulder}=267$ mµ ($\epsilon=6,500$) in 0.1N aqueous sodium bicarbonate solution, (b) with 940 mg (4.5 mmols) of D-α-amino-(1,4-cyclohexadienyl)acetic acid chloride hydrochloride, to obtain 7β-[D-α-amino-α-(1,4-cyclohexadienyl)-acetylamino]-3-methoxy-3-cephem-4-carboxylic acid in the form of the inner salt, melting point 170° (with decomposition); thin layer chromatogram (silica gel; identification with iodine): Rf~0.19 (system: n-butanol/acetic acid/water, 67:10:23) and Rf~0.58 (system: isopropanol/formic acid/water, 77:4:19); ultraviolet absorption spectrum: $\lambda_{max}=267$ mµ ($\epsilon=6,300$) in 0.1N hydrochloric acid, and $\lambda_{max}=268$ mµ ($\epsilon=6,600$) in 0.1N aqueous sodium bicarbonate solution, $[\alpha]_D^{20}=+88°\pm1°$ (c=1.05; 0.1N hydrochloric acid), and (c) with 800 mg (3.6 mmols) of D-α-amino-4-hydroxyphenylacetic acid chloride hydrochloride, to obtain 7β-[D-α-amino-α-(4-hydroxyphenyl)-acetylamino]-3-methoxy-3-cephem-4-carboxylic acid in the form of the inner salt, melting point=243°-244.5° C. (sintering starts from 231°) (with decomposition); thin layer chromatogram (silica gel; identification with iodine): Rf~0.24 (system: n-butanol/acetic acid/water, 67:10:23) and Rf~0.57 (system: isopropanol/formic acid/water, 77:4:19); ultraviolet absorption spectrum: $\lambda_{max}=228$ mµ ($\epsilon=12,000$) and 271 mµ ($\epsilon=6,900$) in 0.1N hydrochloric acid, and $\lambda_{max}=227$ mµ ($\epsilon=10,500$) and $\lambda_{shoulder}=262$ mµ ($\epsilon=8,000$) in 0.1N aqueous sodium bicarbonate solution, $[\alpha]_D^{20}=+165°\pm1°$ (c=1.3; 0.1N hydrochloric acid).

EXAMPLE 7

The compounds which follow can be manufactured analogously from suitable intermediate products obtainable according to the invention:

7β-phenoxyacetamido-3-hydroxy-3-cephem-4-carboxylic acid diphenylmethyl ester,

7β-phenylacetamido-3-hydroxy-3-cephem-4-carboxylic acid diphenylmethyl ester,

7β-amino-3-hydroxy-3-cephem-4-carboxylic acid diphenylmethyl ester,

7β-[D-α-tert.-butoxycarbonylamino-α-phenylacetylamino]-3-hydroxy-3-cephem-4-carboxylic acid diphenylmethyl ester, 7β-(5-benzoylamino-5-diphenylmethoxycarbonylvalerylamino)-3-hydroxy-3-cephem-4-carboxylic acid diphenylmethyl ester, 7β-[D-α-tert.-butoxycarbonylamino-α-(4-hydroxyphenyl)acetylamino]-3-hydroxy-3-cephem-4-carboxylic acid diphenylmethyl ester, 7β-[D-α-tert.-butoxycarbonylamino-α-(2-thienyl)acetylamino]-3-hydroxy-3-cephem-4-carboxylic acid diphenylmethyl ester, 7β-[D-α-tert.-butoxycarbonylamino-α-(3-thienyl)acetylamino]-3-hydroxy-3-cephem-4-carboxylic acid diphenylmethyl ester, 7β-[D-α-tert.-butoxycarbonylamino-α-(2-furyl)acetylamino-3-hydroxy-3-cephem-4-carboxylic acid diphenylmethyl ester, 7β-[D-α-tert.-butoxycarbonylamino-α-(4-isothiazolyl)acetylamino]-3-hydroxy-3-cephem-4-carboxylic acid diphenylmethyl ester, 7β-[D-α-tert.-butoxycarbonylamino-α-(1,4-cyclohexadienyl)-adetylamino]-3-hydroxy-3-cephem-4-carboxylic acid diphenylmethyl ester, 7β-(2-thienyl)-acetylamino-3-hydroxy-3-cephem-4-carboxylic acid diphenylmethyl ester, 7β-(1-tetrazolyl)-acetylamino-3-hydroxy-3-cephem-4-carboxylic acid diphenylmethyl ester, 7β-(4-pyridylthio)-acetylamino-3-hydroxy-3-cephem-4-carboxylic acid diphenylmethyl ester, 7β-(4-aminopyridinium-acetylamino)-3-hydroxy-3-cephem-4-carboxylic acid diphenylmethyl ester, and 7β-[D-α-(2,2,2-trichloroethoxycarbonyloxy)-α-phenylacetylamino]-3-hydroxy-3-cephem-4-carboxylic acid diphenylmethyl ester and corresponding compounds esterified at the 3-hydroxyl group, for example 3-methoxy-7β-phenoxyacetamido-3-cephem-4-carboxylic acid diphenylmethyl ester, 3-methoxy-7β-phenylacetamido-3-cephem-4-carboxylic acid diphenylmethyl ester, 3-methoxy-7β-amino-3-cephem-4-carboxylic acid diphenylmethyl ester and salts thereof, 3-methoxy-7β-phenylacetylamino-3-cephem-4-carboxylic acid or salts thereof, 3-methoxy-7β-(D-α-tert.-butoxycarbonylamino-α-phenylacetylamino)-3-cephem-4-carboxylic acid diphenylmethyl ester, 3-methoxy-7β-(D-α-phenylglycylamino)-3-cephem-4-carboxylic acid or salts thereof, 3-n-butoxy-7β-phenylacetylamino-3-cephem-4-carboxylic acid diphenylmethyl ester, 3-n-butoxy-7β-(D-α-tert.-butoxycarbonylamino-α-phenylacetylamino)-3-cephem-4-carboxylic acid diphenylmethyl ester, 3-n-butoxy-7β-(D-α-phenylglycylamino)-3-cephem-4-carboxylic acid or salts thereof, 3-methoxy-7β-phenylacetylamino-3-cephem-4-carboxylic acid methyl ester, 3-ethoxy-7β-(D-α-tert.-butoxycarbonylamino-α-phenylacetylamino)-3-cephem-4-carboxylic acid diphenylmethyl ester, 3-ethoxy-7β-(D-α-phenylglycylamino)-3-cephem-4-carboxylic acid or salts thereof, 3-benzyloxy-7β-(D-α-tert.-butoxycarbonylamino-α-phenylacetylamino)-3-cephem-4-carboxylic acid diphenylmethyl ester, 3-benzyloxy-7β-(D-α-phenylglycylamino)-3-cephem-4-carboxylic acid or salts thereof, 7β-(5-benzoylamino-5-diphenylmethoxycarbonyl-valerylamino)-3-methoxy-3-cephem-4-carboxylic acid diphenylmethyl ester, 7β-(D-α-tert.-butoxycarbonylamino-α-phenylacetylamino)-3-methoxy-3-cephem-4-carboxylic acid or salts thereof, 7β-[D-α-tert.-butoxycarbonylamino-α-(2-thienyl)acetylamino]-3-methoxy-3-cephem-4-carboxylic acid diphenylmethyl ester, 7β-[D-α-tert.-butoxycarbonylamino-α-(1,4-cyclohexadienyl)-acetylamino]-3-methoxy-3-cephem-4-carboxylic acid diphenylmethyl ester, 7β-[D-α-amino-α-(1-cyclohexen-1-yl)-acetylamino]-3-methoxy-3-cephem-4-carboxylic acid or salts thereof, 7β-[D-α-tert.-butoxycarbonylamino-α-(4-hydroxyphenyl)acetylamino]-3-methoxy-3-cephem-4-carboxylic acid diphenylmethyl ester, 7β-[D-α-amino-α-(4-hydroxyphenyl)-acetylamino]-3-methoxy-3-cephem-4-carboxylic acid or salts thereof, and 7β-[D-α-tert.-butoxycarbonylamino-α-(4-isothiazoyl)acetylamino]-3-methoxy-3-cephem-4-carboxylic acid diphenylmethyl ester, as well as the corresponding ceph-2-em compounds and the isomer mixtures consisting of the ceph-3-em compounds and the ceph-2-em compounds, as well as the 1-oxides of the corresponding ceph-3-em compounds.

We claim:

1. Process for the manufacture of a compound of the formula

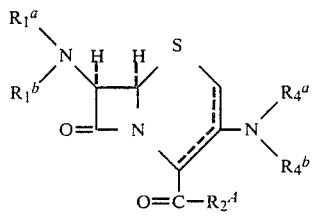

(III)

wherein $R_1^a$ represents an acyl group of the formula

(A$_1$)

wherein $R^I$ represents hydrogen, cyclopentyl, cyclohexyl or cycloheptyl, or such cycloalkyl which is substituted in the 1-position by amino, protected amino, sulphoamino or sulphoamino in the form of an alkali metal salt, or $R^I$ represents phenyl, naphthyl or tetrahydronaphthyl, or phenyl, naphthyl or tetrahydronaphthyl substituted by hydroxyl, protected hydroxyl, and/or by halogen, or $R^I$ represents 4-isoxazolyl, or $R^I$ represents an amino group which is N-substituted by lower alkyl or halogen substituted lower alkyl, or $R_1^a$ represents an acyl group of the formula

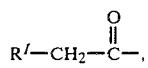

(A$_2$)

wherein $R^I$ represents lower alkyl, halogeno-lower alkyl, phenyloxy-lower alkyl, hydroxyphenyloxy-lower alkyl, protected hydroxyphenyloxy-lower alkyl, halogeno-phenyloxy-lower alkyl, or lower alkyl substituted by amino and/or carboxyl, wherein amino is free or protected and carboxyl is free or protected, or $R^I$ represents lower alkenyl, phenyl, hydroxyphenyl, protected hydroxyphenyl, halogeno-phenyl, hydroxyhalogeno-phenyl, protected hydroxy-halogeno-phenyl, amino-lower alkyl-phenyl, protected amino-lower alkyl-phenyl, phenyloxyphenyl, or $R^I$ represents pyridyl, pyridinium, thienyl, furyl, imidazolyl or tetrazolyl, or these heterocyclic groups substituted by lower alkyl, amino, protected amino, aminomethyl or protected aminomethyl, or $R^I$ represents lower alkoxy, phenyloxy, hydroxy-phenyloxy, protected hydroxyphenyloxy, halogeno-phenyloxy, lower alkylthio, lower alkenylthio, phenylthio, pyridylthio, 2-imidazolylthio, 1,2,4-triazol-3-ylthio, 1,3,4-triazol-2-ylthio, 1,2,4-thiadiazol-3-ylthio, 1,3,4-thiadiazol-2-ylthio, or 5-tetrazolylthio, and these heterocyclylthio groups, substituted by lower alkyl, or $R^I$ represents halogeno, lower alkoxycarbonyl, cyano, carbamoyl, N-lower alkyl-carbamoyl, N-phenylcarbamoyl, lower alkanoyl, benzoyl, or azido, or $R_1^a$ represents an acyl group of the formula

(A$_3$)

wherein $R^I$ represents lower alkyl, phenyl, hydroxyphenyl, protected hydroxyphenyl, halogeno-phenyl, hydroxy-halogenophenyl, protected hydroxy-halogeno-phenyl, furyl, thienyl, or isothiazolyl, and also represents 1,4-cyclohexadienyl, and $R^{II}$ represents amino, protected amino, guanidinocarbonyl-amino, sulphoamino, sulphoamino in alkalimetal salt-form, azido, carboxyl, carboxyl in alkali-metal salt-form, protected carboxyl, cyano, sulpho, hydroxyl, protected hydroxyl, O-lower alkyl-phosphono, O,O'-di-lower alkylphosphono or halogeno, or $R_1^a$ represents a group of the formula

(A$_4$)

wherein $R^I$ and $R^{II}$ each represent halogeno, or lower alkoxycarbonyl, or $R_1^a$ represents a group of the formula

(A$_5$)

wherein $R^I$ represents phenyl, hydroxyphenyl, protected hydroxyphenyl, hydroxy-halogeno-phenyl, protected hydroxyhalogeno-phenyl, furyl, thienyl, isothiazolyl or 1,4-cyclohexadienyl, and $R^{II}$ represents aminomethyl or protected aminomethyl or $R_1^a$ represents a group of the formula

(A$_6$)

wherein each of the groups $R^I$, $R^{II}$ and $R^{III}$ represents lower alkyl, and $R_1^b$ represents hydrogen, or $R_1^a$ and $R_1^b$ together represent 1-oxo-3-aza-1,4-butylen, such group substituted in the 2-position by a group $R^I$ as defined under formula (A$_3$) and such group substituted in the 4-position by lower alkyl, $R_2^A$ represents a group which together with the carbonyl grouping —C(=O)— forms a protected esterified carboxyl group, and the the group —N($R_4^a$)($R_4^b$) denotes a secondary amino group, wherein one of the substituents $R_4^a$ and $R_4^b$ represents hydrogen and the other represents lower alkyl, lower alkoxy-lower alkyl, lower alkyl-thio lower alkyl, cyclohexyl-lower alkyl, phenyl-lower alkyl, thienyl-lower alkyl, cycloalkyl with 3 to 7 carbon atoms, or such cycloalkyl substituted by lower alkyl, lower alkoxy, lower alkylthio, cyclohexyl, phenyl, or furyl, or wherein —N($R_4^a$)($R_4^b$) denotes a tertiary amino group, wherein each of the substituents $R_4^a$ and $R_4^b$, independent of each other is lower alkyl, lower alkoxy-lower alkyl, lower alkylthio-lower alkyl, cyclohexyl-lower alkyl, phenyl-lower alkyl, thienyl-lower alkyl, cycloalkyl with 3 to 7 carbon atoms, or such cycloalkyl substituted by lower alkyl, lower alkoxy, lower alkylthio, cyclohexyl, phenyl, or furyl, or wherein —N($R_4^a$)($R_4^b$) is 1-aziridinyl, 1-pyrrolidinyl, 1-piperidyl, 1H-2,3,4,5,6,7-hexahydroazepinyl, 4-morpholinyl, 4-thiomorpholinyl, 1-piperazinyl, or 4-methyl-1-piperazinyl and in which the double bond can be in the 2,3-position or the 3,4-position or a process giving a mixture of a compound having the double bond in the 2,3-position and a compound having the double bond in the 3,4-position,
characterised in that a compound of the formula

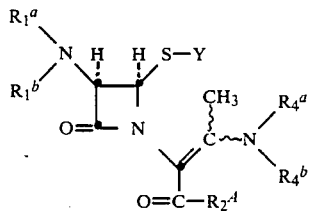 (II)

wherein $R_1^a$, $R_1^b$, $R_2^A$, $R_4^a$ and $R_4^b$ have the meanings mentioned under formula III, and Y represents a leaving group of the formula —S—$R_4$, wherein $R_4$ is a diazacyclyl, oxazacyclyl, thiazacylyl, thiadiazacyclyl, thiatriazacyclyl, oxadiazacyclyl, oxatriazacyclyl, benzdiazacyclyl, benzoxazacyclyl or benzthiazacyclyl radical of aromatic character which radical is bonded to the thio group —S— by one of its ring carbon atoms, which is bonded to a ring nitrogen atom by a double bond, or such group substituted by lower alkyl, lower alkoxy, halogen or phenyl, or wherein $R_4$ denotes lower alkanoyl, lower thioalkanoyl, cycloalkane carbonyl, cycloalkanethio carbonyl, benzoyl, thiobenzoyl, naphthylcarbonyl, naphthylthiocarbonyl, pyridylcarbonyl, thenoyl, furoyl, pyridylthiocarbonyl, thiothenoyl or thiofuroyl, or represents such an acyl or thioacyl group which is monosubstituted or polysubstituted by lower alkyl, halogen, lower alkoxy, phenyl or phenyloxy, which groups $R_4$ have up to 18 carbon atoms, or Y represents a leaving group of the formula —$SO_2$—$R_5$, wherein $R_5$ represents unsubstituted or lower alkoxy-, halogeno-, phenyl-, or phenyloxy-monosubstituted or -polysubstituted lower alkyl, lower alkenyl, cyclopentyl or cyclohexyl or $R_5$ represents naphthyl, or phenyl, or naphthyl or phenyl monosubstituted or polysubstituted by lower alkyl, lower alkoxy, halogen, phenyl, phenyloxy, or nitro, which groups $R_5$ have up to 18 carbon atoms, is heated in an inert solvent at a temperature of between 20° and 150°.

2. Process according to claim 1, characterised in that $R_1^a$ represents an acyl group of the formula ($A_2$) or ($A_3$) and $R_1^b$ represents hydrogen.

3. Process according to claim 1, characterised in that $R_1^a$ represents phenylacetyl, phenyloxyacetyl or D-α-tert.-butyloxycarbonylamino-α-phenylacetyl and $R_1^b$ represents hydrogen.

4. Process according to claim 1, characterised in that $R_2^A$ represents benzyloxy, p-nitrobenzyloxy, diphenylmethoxy, lower alkoxy, 2-halogeno-lower alkoxy, or halogen.

5. Process according to claim 1, characterised in that $R_1^a$ and $R_1^b$ are as defined in claim 1, $R_2^A$ represents benzyloxy, p-nitrobenzyloxy or diphenylmethoxy methoxy, tert.-butoxy, or 2,2,2-trichloroethoxy, one of the radicals $R_4^a$ or $R_4^b$ denotes hydrogen and the other denotes lower alkyl, lower alkyl substituted by lower alkoxy, by lower alkylthio, by cycloalkyl, by phenyl, or by thienyl, cycloalkyl with 3 to 7 carbon atoms, or such cycloalkyl substituted by lower alkyl, by lower alkoxy, by lower alkylthio, by cycloalkyl, by phenyl or by furyl, or wherein —N($R_4^a$)($R_4^b$) denotes dimethylamino, diethylamino, N-methyl-ethylamino, di-isopropylamino, N-methyl-isopropylamino, dibutylamino, N-methyl-isobutylamino, dicyclopropylamino, N-methyl-cyclopropylamino, dicyclopentylamino, N-methyl-cyclopentylamino, dicyclohexylamino, N-methyl-cyclohexylamino, dibenzylamino, N-methyl-benzylamino, N-cyclopropyl-benzylamino, 1-aziridinyl, 1-pyrrolidinyl, 1-piperidyl, 1H-2,3,4,5,6,7-hexahydroazepinyl, 4-morpholinyl, 4-thiomorpholinyl, 1-piperazinyl or 4-methyl-1-piperazinyl, Y is a —S—$R_4$ group, wherein $R_4$ denotes 1-methyl-imidazol-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl, 1-methyl-benzimidazol-2-yl, benzoxazol-2-yl or benzthiazol-2-yl, or wherein $R_4$ denotes lower alkanoyl, lower thioalkanoyl, cycloalkanecarbonyl, cycloalkanethiocarbonyl, benzoyl, thiobenzoyl, naphthylcarbonyl, naphthylthiocarbonyl, 2-, 3- or 4-pyridylcarbonyl, 2- or 3-thenoyl, 2- or 3-furoyl, 2-, 3- or 4-pyridylthiocarbonyl, 2- or 3-thiothenoyl or 2- or 3-thiofuroyl, which acyl or thioacyl group can be monosubstituted or polysubstituted by lower alkyl, halogen, lower alkoxy, phenyl or phenyloxy, or Y is a —$SO_2R_5$ group, wherein $R_5$ is unsubsituted or lower alkoxy-, halogen-, phenyl-, or phenyloxy-, -monosubstituted or -polysubstituted lower alkyl, lower alkenyl, cyclopentyl or cyclohexyl, naphthyl or phenyl, or phenyl monosubstituted or polysubstituted by lower alkyl, lower alkoxy, halogen, phenyl, phenyloxy or by nitro.

6. Process according to claim 1, characterised in that $R_4$ denotes 1-methyl-imidazole-2-yl, 1,3-thiazol-2-yl, 1,3,4-thiadiazol-2-yl, 1,3,4,5-thiatriazol-2-yl, 1,3-oxazol-2-yl, 1,3,4-oxadiazol-2-yl, 1,3,4,5-oxatriazol-2-yl, 2-quinolyl or 1-methyl-benzimidazol-2-yl.

7. Process according to claim 1, characterised in that $R_4$ is benzthiazol-2-yl or benzoxazol-2-yl.

8. Process according to claim 1, characterised in that Y is a —$SO_2$—$R_5$ group, wherein $R_5$ is phenyl, or phenyl monosubstituted or polysubstituted by lower alkyl, lower alkoxy, halogen, phenyl, phenyloxy or nitro.

9. Process according to claim 1, characterised in that Y denotes a —$SO_2$—$R_5$ group, wherein $R_5$ is p-tolyl.

10. Process according to claim 1, characterised in that —N($R_4^a$)($R_4^b$) represents pyrrolidino, N-methylcyclohexylamino, or cyclohexylamino.

11. Process according to claim 1, characterised in that —N($R_4^a$)($R_4^b$) represents 4-morpholino.

12. Process according to claim 1, characterised in that the 7β-phenoxyacetamido-3-pyrrolidino-3-cephem-4-carboxylic acid p-nitrobenzylester, the corresponding 2-cephem ester or a mixture thereof is manufactured.

13. Process according to claim 1, characterised in that the 7β-phenoxyacetamido-3-cyclohexylamino-3-cephem-4-carboxylic acid p-nitrobenzylester, the corresponding 2-cephem ester or a mixture thereof is manufactured.

14. Process according to claim 1, characterised in that the 7β-phenoxyacetamido-3-pyrrolidino-3-cephem-4-carboxylic acid diphenylmethylester, the corresponding 2-cephem ester or a mixture thereof is manufactured.

* * * * *